(12) United States Patent
Pourgholami et al.

(10) Patent No.: US 10,053,422 B2
(45) Date of Patent: Aug. 21, 2018

(54) COMPOUNDS FOR THE TREATMENT OF MTOR PATHWAY RELATED DISEASES

(71) Applicant: Pitney Pharmaceuticals Pty Limited, Claremont (AU)

(72) Inventors: Mohammad Hossein Pourgholami, Penshurst (AU); David L. Morris, Lugarno (AU); Roger Aston, Kogarah (AU)

(73) Assignee: Pitney Pharmaceuticals Pty Limited, Kogarah (AU)

( * ) Notice: Subject to any disclaimer, the term of this patent is extended or adjusted under 35 U.S.C. 154(b) by 0 days.

(21) Appl. No.: 15/613,635

(22) Filed: Jun. 5, 2017

(65) Prior Publication Data
US 2017/0369435 A1 Dec. 28, 2017

Related U.S. Application Data

(62) Division of application No. 14/420,081, filed as application No. PCT/AU2013/000859 on Aug. 5, 2013, now Pat. No. 9,790,176.

(30) Foreign Application Priority Data

Aug. 6, 2012 (AU) .............................. 2012903365

(51) Int. Cl.
| | | |
|---|---|---|
| *A61K 31/275* | (2006.01) | |
| *C07C 255/00* | (2006.01) | |
| *C07C 323/62* | (2006.01) | |
| *A61K 31/277* | (2006.01) | |
| *C07C 255/62* | (2006.01) | |
| *C07C 317/44* | (2006.01) | |
| *C07C 255/29* | (2006.01) | |

(52) U.S. Cl.
CPC .......... *C07C 323/62* (2013.01); *A61K 31/277* (2013.01); *C07C 255/29* (2013.01); *C07C 255/62* (2013.01); *C07C 317/44* (2013.01)

(58) Field of Classification Search
CPC .. A61K 31/277; C07C 255/29; C07C 255/62; C07C 317/44; C07C 323/62
USPC ...................... 514/1, 521, 522; 558/392, 415
See application file for complete search history.

(56) References Cited

U.S. PATENT DOCUMENTS

| | | | |
|---|---|---|---|
| 8,835,478 B2 | 9/2014 | Morris et al. | |
| 9,308,193 B2 | 4/2016 | Morris | |
| 9,790,176 B2* | 10/2017 | Pourgholami | ........ C07C 317/44 |
| 9,833,431 B2* | 12/2017 | Morris | ................ A61K 31/277 |
| 2015/0166477 A1 | 6/2015 | Pourgholami et al. | |
| 2016/0220527 A1 | 8/2016 | Morris | |
| 2016/0228399 A1 | 8/2016 | Morris et al. | |

FOREIGN PATENT DOCUMENTS

| | | |
|---|---|---|
| EP | 1445251 | 8/2004 |
| WO | 0249641 | 6/2002 |

OTHER PUBLICATIONS

Dazed et al., "mTOR signaling in disease", 2011, Current Opinion in Cell Biology, 23(6), pp. 744-755. (Year: 2011).*
Tiwari et al., "The potential role of neuroinflammation and transcription factors in Parkinson disease", 2017, Dialogues Clin. Neurosci., 19(1), pp. 71-80. (Year: 2017).*
U.S. Appl. No. 14/420,081, "Non-Final Office Action", dated Sep. 26, 2016, 23 pages.
U.S. Appl. No. 14/420,081, "Notice of Allowance", dated Jun. 9, 2017, 7 pages.
U.S. Appl. No. 14/420,081, "Restriction Requirement", dated Mar. 15, 2016, 8 pages.
Ducray et al., "Discovery of amino-acetonitrile derivatives, a new class of synthetic anthelmintic compounds", Bioorganic and Medicinal Chemistry Letters vol. 18, No. 9, 2008, pp. 2935-2938.
Karadzovska et al., "Pharmacokinetics of monepantel and its sulfone metabolite, monepantel sulfone, after intravenous and oral administration in sheep", Journal of Veterinary Pharmacology & Therapeutics, vol. 32, No. 4, Aug. 2009, pp. 359-367.
PCT/AU2013/000859, "International Preliminary Report on Patentability", dated May 27, 2014, 53 pages.
PCT/AU2013/000859, "International Search Report and Written Opinion", dated Aug. 30, 2013, 12 pages.
Stuchlikova et al., "Investigation of the Metabolism of Monepantel in Ovine Hepatocytes by UHPLC/MS/MS", nalytical and Bioanalytical Chemistry, vol. 405, No. 5, 2013, pp. 1705-1712.

* cited by examiner

*Primary Examiner* — My-Chau T. Tran
(74) *Attorney, Agent, or Firm* — Kilpatrick Townsend & Stockton LLP

(57) ABSTRACT

The present invention relates to compounds for the treatment of mTOR (mammalian Target Of Rapamycin) pathway related diseases. Specifically, the present invention relates to the use of aminoacetonitrile derivatives (AADs) in the treatment of mTOR pathway related diseases.

19 Claims, 35 Drawing Sheets

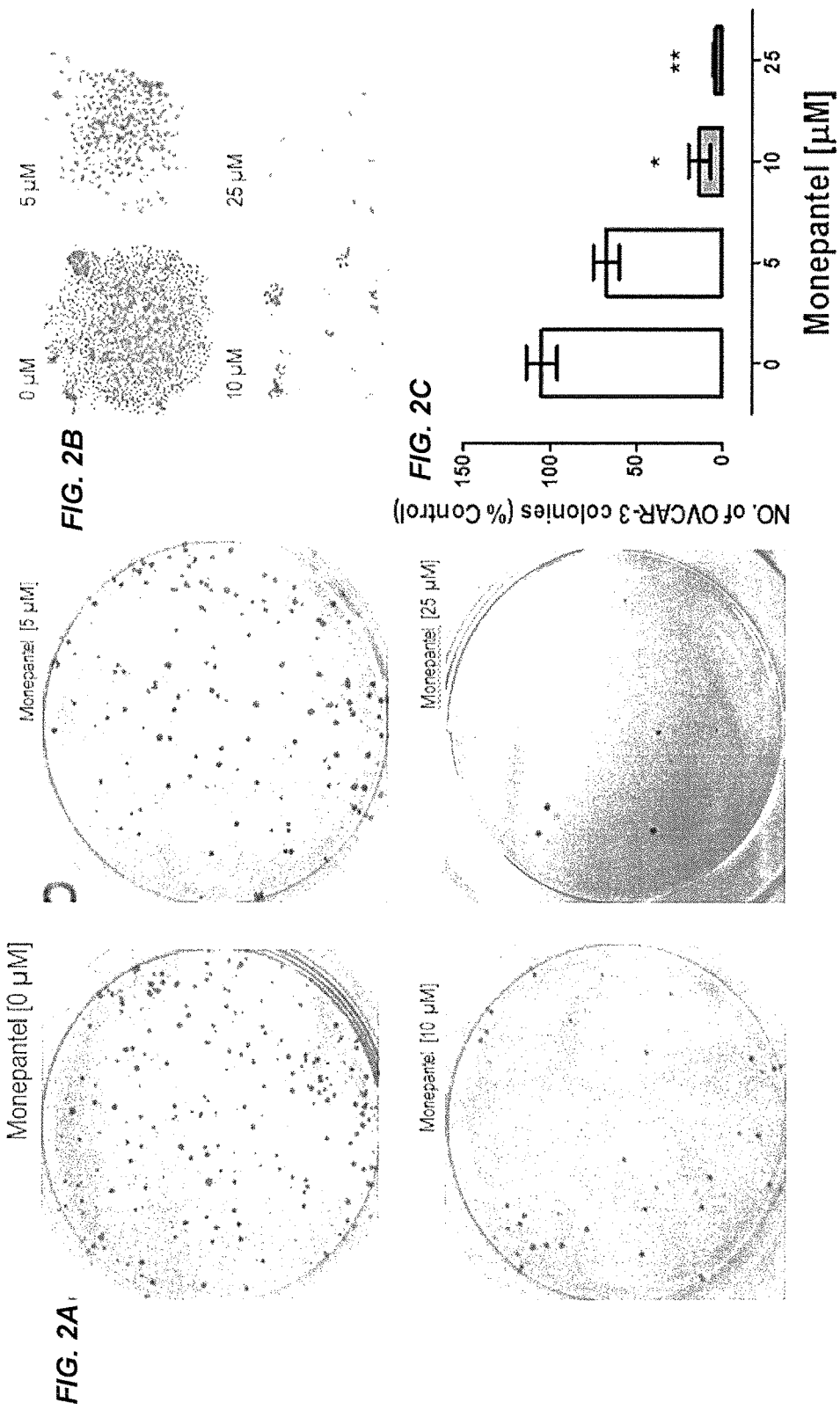

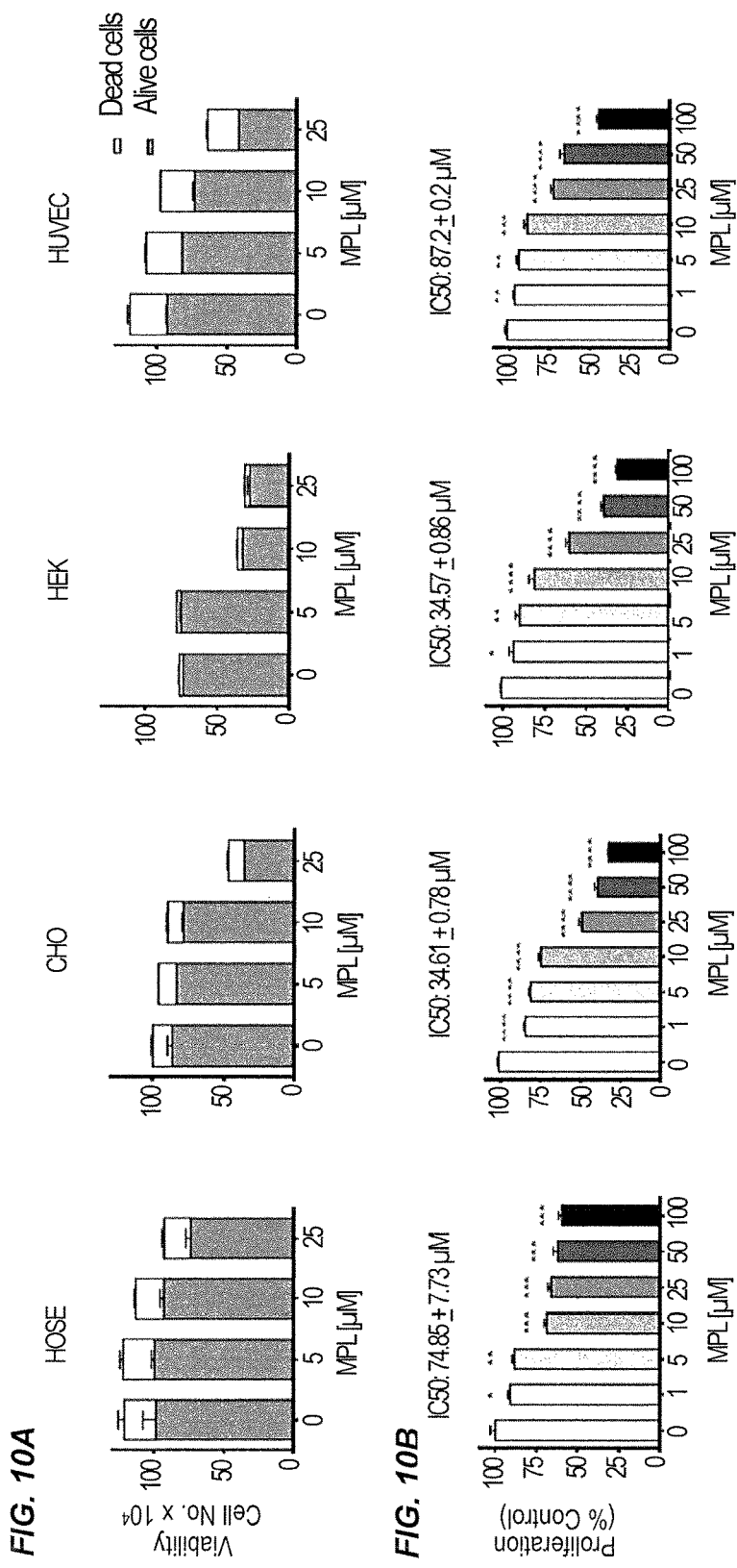

**** P value: <0.0001

*** P value: 0.0003

No star P value: 0.0699

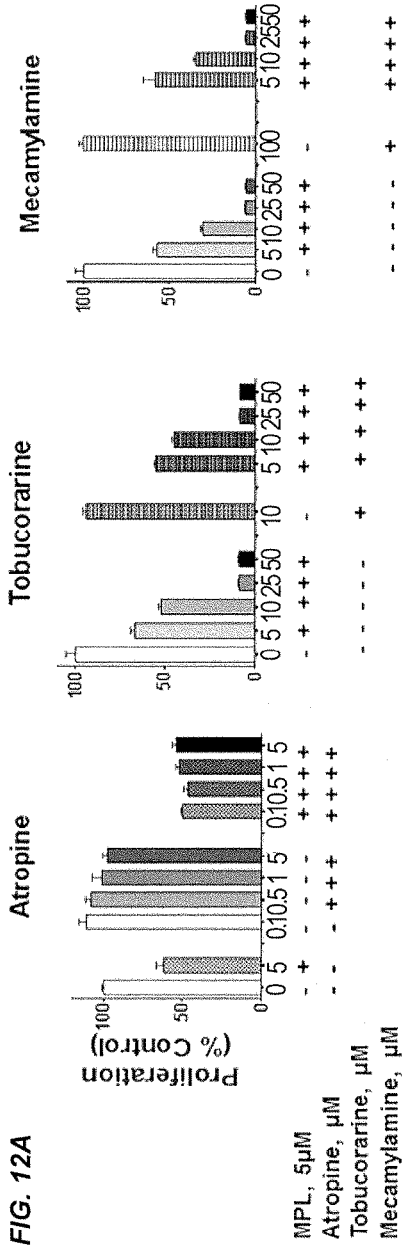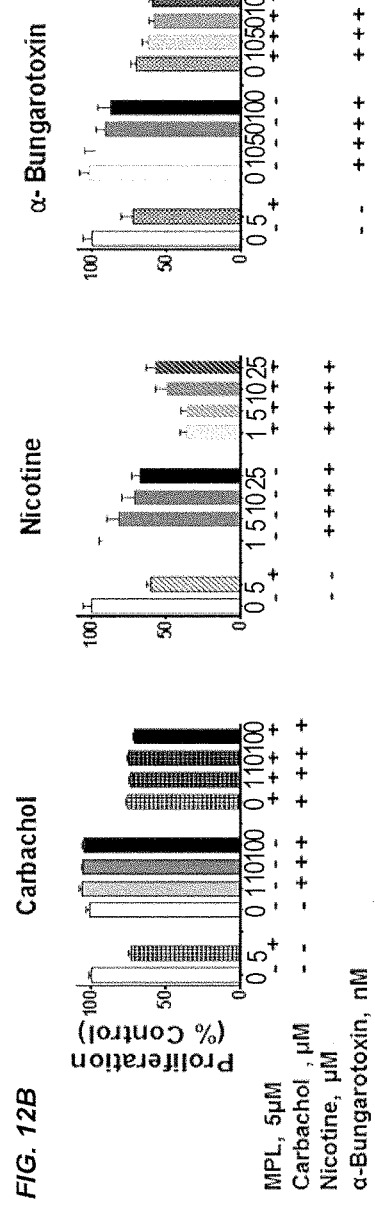
FIG. 12A
FIG. 12B
A: Atropine: muscarinic Ach. Receptor antagonist. Tobucorarine: nicotinic Ach. Receptor antagonist. Mecamylamine: nonselective, noncompetitive nicotinic receptor antagonist
B: Carbachol: muscarinic nicotinic ach. receptor agonist. Nicotine: Nicotinic ach. receptor agonist. Alpha-bungarotoxin: selective α7 nicotinic ach receptor agonist

COMPOUNDS FOR THE TREATMENT OF MTOR PATHWAY RELATED DISEASES

CROSS-REFERENCE TO RELATED APPLICATIONS

This application is a divisional of U.S. patent application Ser. No. 14/420,081, filed, Feb. 6, 2015, which is a U.S. national stage of PCT/AU2013/000859, filed Aug. 5, 2013, which claims the benefit of priority to Australian Patent Application No. 2012903365 filed Aug. 6, 2012, the disclosures of which are incorporated herein by reference in their entirety.

TECHNICAL FIELD

In general, the present invention relates to compounds for the treatment of mTOR (mammalian Target Of Rapamycin) pathway related diseases. Specifically, the present invention relates to the use of aminoacetonitrile derivatives (AADs) in the treatment of mTOR pathway related diseases.

BACKGROUND

Aminoacetonitrile derivatives (AADs) are a class of anthelmintics effective against drug-resistant nematodes. The nematodes, or roundworms, comprise a large number of pathogens of man and domestic animals. Gastrointestinal nematodes, such as *Haemonchus contortus*, are major parasites of ruminants that cause substantial economic losses to livestock production worldwide.

Monepantel (MPL) (N-[(1S)-1-Cyano-2-(5-cyano-2-trifluoromethyl-phenoxy)-1-methyl-ethyl]-4-trifluoromethyl-sulfanyl-benzamide) is an example of such an AAD and has been approved as a nematocide for the treatment of sheep gastrointestinal parasites.

MPL

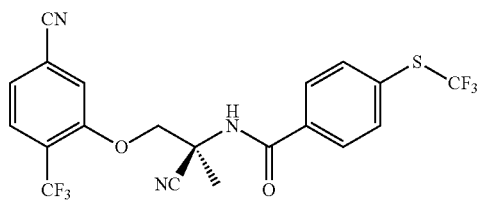

MPL has been shown to be efficacious against various species of livestock-pathogenic nematodes.

As a nematocide, the mechanism of action of MPL is via ligand-gated ion channels leading to interference of signal transduction at neuromuscular synapse. The affected parasites will then experience dysregulation in muscle contraction, paralysis, necrosis and moulting defects. Three nicotinic acetylcholine receptor (nAChR) related genes have been identified as the primary targets of MPL and all of the three genes encode for the proteins representing the DEG-3 subfamily of nAChR subunits that are only present in nematodes. The DEG-3 gene encodes a nAChR α-subunit which holds resemblance to that of α7 subunit in second transmembrane domain.

It has now surprisingly been found that AADs also bind to mTOR pathway target (receptors) in mammalian cells and as such are effective in the treatment of mTOR pathway related diseases.

SUMMARY OF THE INVENTION

According to a first aspect of the present invention there is provided a compound of formula (I):

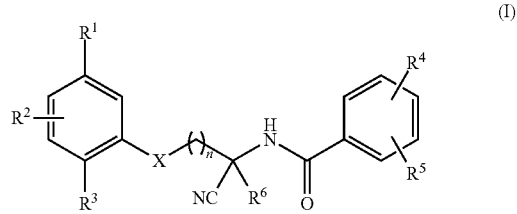

(I)

or a metabolite, pharmaceutically acceptable salt, solvate or prodrug thereof, for the treatment of one or more mTOR pathway related diseases, wherein, $R^1$, $R^2$ and $R^3$ and $R^5$ are each independently selected from H, alkyl, halogen, —$CF_3$ or —CN;

$R^4$ and $R^6$ are each independently selected from H, alkyl, halogen, alkoxy, —$CF_3$, —$OCF_3$, —$SO_2CF_3$, —$SOCF_3$ or —$SCF_3$;

X is a heteroatom, N(alkyl) or NH; and n is 1 to 20.

According to a second aspect of the present invention, there is provided a method for the treatment of one or more mTOR pathway related diseases, the method comprising administering a therapeutically effective amount of a compound of formula (I) according to the first aspect of the invention, or a metabolite, pharmaceutically acceptable salt, solvate or prodrug thereof, to a patient in need thereof.

According to a third aspect of the present invention, there is provided use of a compound of formula (I), or a metabolite, pharmaceutically acceptable salt, solvate or prodrug thereof, according to the first aspect of the invention, for the manufacture of a medicament for the treatment of one or more mTOR pathway related diseases.

According to a fourth aspect of the present invention, there is provided a compound of formula (I) according to the first aspect of the invention for use in the treatment of one or more mTOR pathway related diseases, wherein the disease is not cancer.

According to a fifth aspect of the present invention, there is provided a method for the treatment of one or more mTOR pathway related diseases, wherein the disease is not cancer, the method comprising administering a therapeutically effective amount of a compound of formula (I) according to the first aspect of the invention, or a metabolite, pharmaceutically acceptable salt, solvate or prodrug thereof, to a patient in need thereof.

According to a sixth aspect of the present invention, there is provided use of a compound of formula (I), or a metabolite, pharmaceutically acceptable salt, solvate or prodrug thereof, according to the first aspect of the invention, for the manufacture of a medicament for the treatment of one or more mTOR pathway related diseases, wherein the disease is not cancer.

Preferably, $R^1$ is —CN, H or halogen. More preferably, $R^1$ is —CN. Preferably, $R^2$ is H or halogen, and more preferably H. Preferably, $R^3$ is —$CF_3$ or halogen and more preferably —$CF_3$. Preferably, $R^4$ is —$SCF_3$, —$SOCF_3$, —$SO_2CF_3$, —$OCF_3$ or —$CF_3$. More preferably, $R^4$ is —$SCF_3$ or —$SO_2CF_3$. Preferably, $R^5$ is H. Preferably, $R^6$ is alkyl and more preferably $CH_3$. Preferably, X is O. Preferably, n is 1 to 15, 1 to 10, 1 to 5, 1 to 2, or 1. Most preferably, n is 1. Preferably, $R^4$ is arranged para to the amide moiety.

The compound of formula (I) may be the (R)- or (S)-enantiomer or the racemate. Preferably, the compound of formula (I) is the (S)-enantiomer.

The compound of formula (I) may be selected from any one of the following compounds:

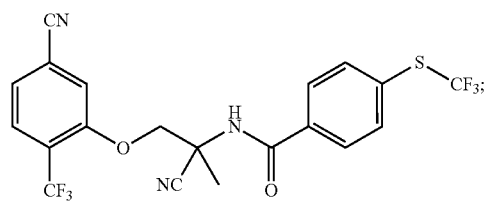

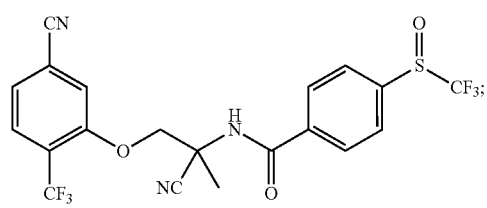

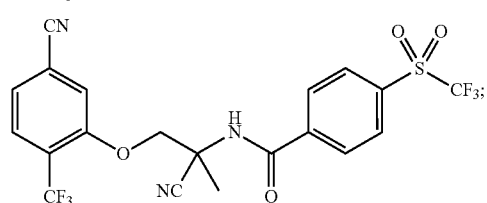

AAD 450
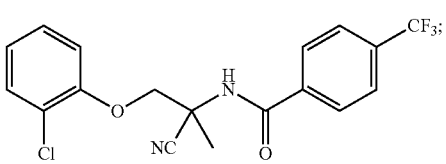

AAD 907
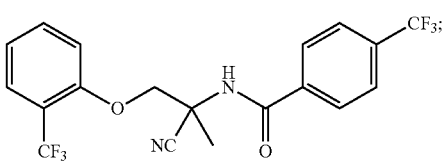

AAD 970
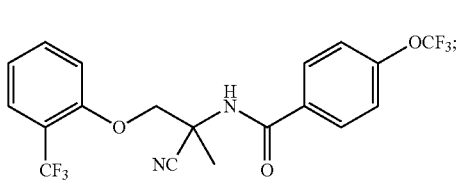

AAD 1154
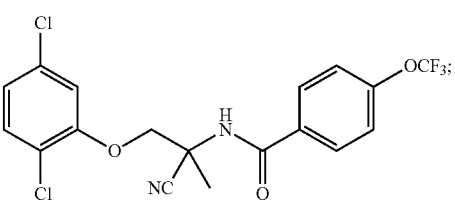

AAD 004
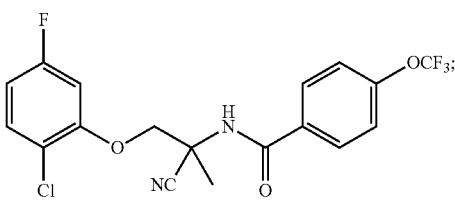

AAD 2009
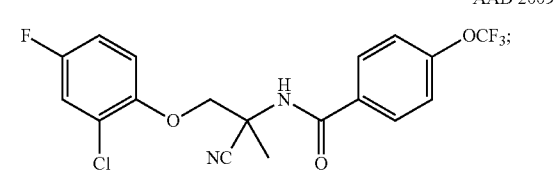

AAD 1336
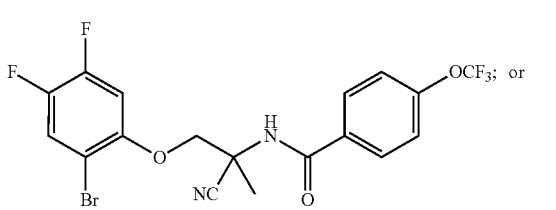

AAD 1470
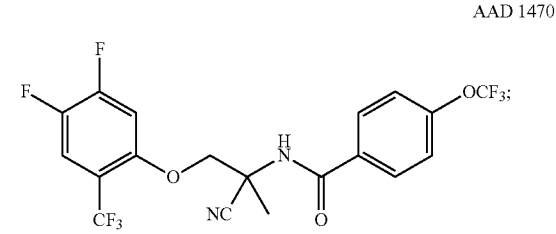

wherein each of the above compounds is the (R)- or (S)-enantiomer, or the racemate, or a metabolite, pharmaceutically acceptable salt, solvate or prodrug thereof.

Preferably, the compound of formula (I) may be selected from any one of the following compounds:

AAD 2224 (MPL-(R))
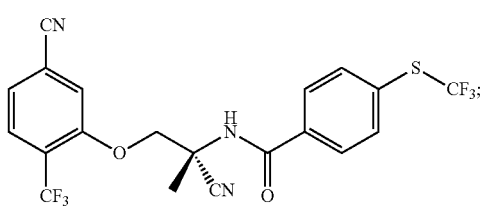

AAD 907
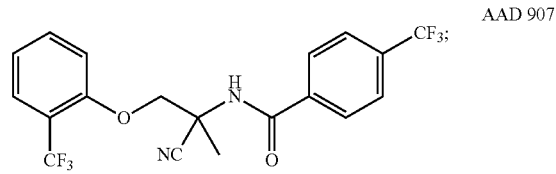

-continued

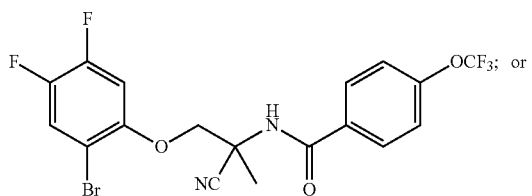
AAD 1336

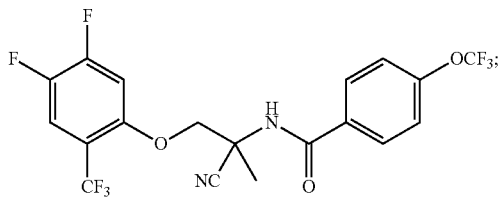
AAD 1470 wherein each of the above compounds is the (R)- or (S)-enantiomer, or the racemate, (unless specified) or a metabolite, pharmaceutically acceptable salt, solvate or prodrug thereof.

More preferably, the compound of formula (I) is MPL (N-[(1S)-1-cyano-2-(5-cyano-2-trifluoromethyl-phenoxy)-1-methyl-ethyl]-4-trifluoromethylsulfanyl-benzamide):

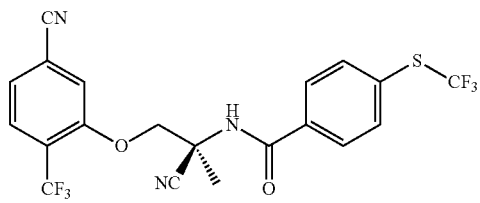
MPL or a metabolite, pharmaceutically acceptable salt, solvate or prodrug thereof.

Further, the compound of the invention may be a metabolite of MPL, which is monepantel sulphone (MPL-SO$_2$):

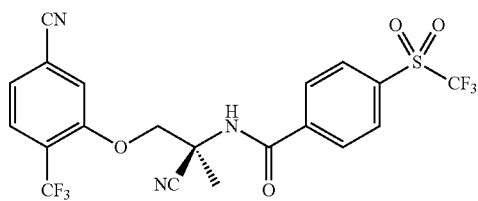
MPL-SO$_2$ or a metabolite, pharmaceutically acceptable salt, solvate or prodrug thereof.

Preferably, the one or more mTOR pathway related diseases is selected from Alzheimer's disease, Huntington's disease, age-related diseases, diseases related to transplant rejection, chronic inflammatory diseases, diseases related to glycogen storage, cancer, metastasis, systemic lupus, diseases related to inflammation and immune activation, anaemia, leucopenia, thrombocytopenia, diseases related to stent coatings, renal insufficiency, obesity, diabetes/insulin resistance, diseases related to non-alcoholic fatty liver, polycystic kidney, Parkinson's disease and fibrosis. Preferably, the mTOR pathway related disease is chronic inflammatory disease, which may be rheumatoid arthritis. Preferably, the fibrosis is fibrosis of the liver, cardiac fibrosis or pulmonary fibrosis. Most preferably the diseases to be treated are cancer and metastasis. Preferably, the cancer is associated with a kinase. Preferably, the kinase is a cyclin-dependent kinase, and more preferably, cdk2 or cdk4.

Preferably, the cancer is selected from the following: carcinoma, including that of the bladder, breast, colon, mesothelioma, kidney, liver, lung, including small cell lung cancer, non-small cell lung cancer, head and neck, oesophagus, gall bladder, ovary, pancreas, stomach, cervix, thyroid, prostate, and skin, including squamous cell carcinoma; hematopoietic tumors of lymphoid lineage, including leukaemia, acute lymphocytic leukaemia, acute lymphoblastic leukaemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoietic tumors of myeloid lineage, including acute and chronic myelogenous leukemias, myelodysplastic syndrome and promyelocyte leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Preferably, the cancer to be treated is selected from cancer of the ovaries, breast, prostate or mesothelioma cancer, and most preferably the cancer to be treated is cancer of the ovaries.

In a further aspect of the invention, the compounds of formula (I) may be used in the treatment of one or more mTOR pathway related diseases, wherein the disease is not cancer.

Preferably, the one or more mTOR pathway related diseases is selected from Alzheimer's disease, Huntington's disease, age-related diseases, diseases related to transplant rejection, chronic inflammatory diseases, diseases related to glycogen storage, metastasis, systemic lupus, diseases related to inflammation and immune activation, anaemia, leucopenia, thrombocytopenia, diseases related to stent coatings, renal insufficiency, obesity, diabetes/insulin resistance, diseases related to non-alcoholic fatty liver, polycystic kidney, Parkinson's disease and fibrosis.

Preferably, the mTOR pathway related disease is chronic inflammatory disease, which may be rheumatoid arthritis or organ rejection after transplant.

BRIEF DESCRIPTION OF THE FIGURES

FIG. 2A, FIG. 2B, and FIG. 2C show the effect of MPL on the colony formation activity of OVCAR-3 cells. Following incubation of cells with MPL (0, 5, 10 and 25 µmol/L) for 72 hours, cells were washed, transferred to agar plates, cultured with their regular growth medium and incubated under standard conditions for 2 weeks. Cells were then fixed with 100% methanol and stained with 1% crystal violet. Colonies (a cluster of cells greater than 50) were counted under a microscope (magnification ×5). The number of colonies counted for different experimental groups is expressed as a percentage of the control.

FIG. 9A) Microscopic image of OVCAR-3 cells exposed to MPL (0, 5, 10, 25 µM) for 72 h. Human ovarian cancer cell lines OVCAR-3, A2780, SKOV-3, IGROV-1 were cultured in the presence of MPL (0, 5, 10, 25, µmol/L) for 72 h. Effect of MPL on cell viability was assessed using the standard Trypan blue assay. Control (vehicle treated) cells were taken to present 100% viable and the MPL treated groups are expressed as percentage of control. Each drug concentration was tested in quadruplicate and each experiment was repeated at least twice. The data (mean±SEM are presented as % control (FIG. 9B). For statistical comparisons, each drug treated group was compared with the control group using Student's t test and a p value of 0.5 or less was considered to present a significant change (p<0 . . . 5), *=<0.05, <0.01, *=p<0.001.

FIG. 10A and FIG. 10B show the effect of MPL on the viability of normal cells and shows the anti-proliferative effect of MPL is cancer cell orientated. Normal cells HOSE, CHO, HEK and HUVEC were cultured in the presence of MPL (0, 5, 10, 25, µmol/L) for 72 h. Effect of MPL on cell viability was assessed using the standard Trypan blue assay. Results are presented as mean±SEM compared to control (100%).

FIG. 12A and FIG. 12B show that the MPL antiproliferative effect is independent of nicotinic receptors. Cells were pre-treated (30 min) with increasing concentrations of nicotine, carbachol or the receptor antagonists, atropine, mecamylamine, tubocurarine, and α-bungarotoxin. MPL (5 µM) was added and left in the cell culture incubator for 72 h. Each drug concentration was tested in quadruplicate and each experiment was repeated twice. Combine values (mean±SEM) are presented as % control.

FIGS. 20-22 in general show the effect of MPL on s.c. xenografts in female nude mice. Mice were inoculated in the left flank with 2.5 million log-phase growing human OVCAR-3 cells. Tumor growth was monitored by caliper measurements and tumor volumes were determined through measuring orthogonal diameters. Estimated tumor volume was calculated based on the formula ½ (Length×Width2), where width is the shorter of the two orthogonal measurements. Treatment was initiated 7 days post tumor cell injection before which, mice were randomized and assigned to treatment or the control group (5-6 per group). Monepantel suspended in 0.5% HPMC was administered i.p. at 2.5 or 25 mg/kg (FIG. 19), 25 and 50 mg/kg (FIG. 20) or orally at 50 and 100 mg/kg, all given three times weekly. Control group mice received similar volume of 0.5% HPMC in an exactly similar manner and time.

DEFINITIONS

Figure 1:
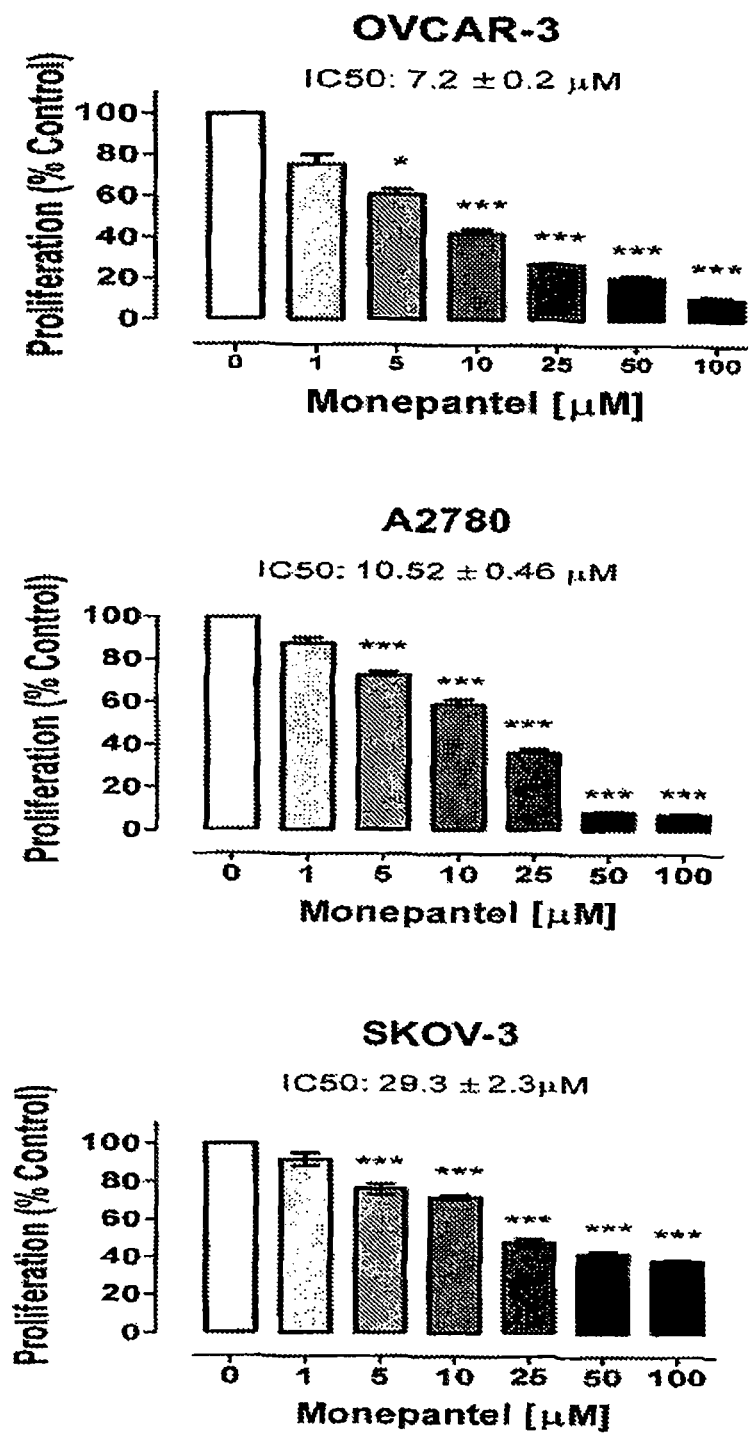
FIG. 1 shows the inhibition of cell proliferation by MPL. Ovarian cancer cell lines OVCAR-3, A2780 and SKOV-3 and normal HUVEC (control) were all cultured in the presence of MPL (0, 1, 5, 10, 25, 50 and 100 µmol/L) for 72 hours. The effect of MPL on cell proliferation was assessed using the SRB assay. Control (vehicle treated) cells were taken to present 100% proliferation and the MPL treated groups are expressed as percentage of control. Each drug concentration was tested in quadruplicate and each experiment was repeated at least twice. The data (mean±SEM) are presented as a percentage of the control. For statistical comparisons, each drug treated group was compared with the control group using Student's t test.

"Halogen" means fluorine, chlorine, bromine or iodine, preferably fluorine or chlorine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Aryl" by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl. The term "aryl" also includes fused cyclic hydrocarbon rings which are partially aromatic (i.e., one of the fused rings is aromatic and the other is non-aromatic). An exemplary aryl group which is partially aromatic is indanyl.

"Heteroaryl," by itself or as part of another substituent, means a cyclic or polycyclic group having from five to twelve ring atoms selected from C, N, O and S, wherein at least one ring heteroatom is O, N or S, and wherein at least one of the constituent rings is aromatic. Exemplary heteroaryl groups for use in the invention include carbazolinyl, carbolinlyl, chromenyl, cinnolinyl, furanyl, benzofuranyl, benzofurazanyl, isobenzofuranyl, imidazolyl, benzimidazolyl, benzimidazolonyl, indazolyl, indolyl, isoindolyl, indolinyl, indolazinyl, indynyl, oxadiazolyl, oxazolyl, benzoxazolyl, isoxazolyl, pyranyl, pyrazinyl, pyrazolyl, benzopyrazolyl, pyridazinyl, pyridyl, pyrimidinyl, pyrrolyl, quinolyl, isoquinolyl, tetrazolyl, thiazolyl, isothiazolyl, thiadiazolyl, thienyl, benzothioenyl, benzothiazolyl, quinoxalinyl, triazinyl and triazolyl, and N-oxides thereof.

One subgroup of heteroaryl groups have 5 ring atoms. Exemplary heteroaryl groups in this embodiment are pyrazolyl, pyridyl, thiazolyl and imidazolyl.

Another subgroup of heteroaryl groups have 6 ring atoms. Exemplary heteroaryl groups in this embodiment are pyridinyl and pyrimidinyl.

The term "heteroaryl" also includes fused cyclic heterocyclic rings which are partially aromatic (i.e., one of the fused rings is aromatic and the other is non-aromatic). An exemplary heteroaryl group which is partially aromatic is benzodioxol.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

"Heteroatom" means an atom selected from N, O, P and S. Where necessary, any undesignated valency is independently selected from H, OH, carbonyl, n-alkyl or alkoxy.

"n" may be 1 to 20, preferably 1 to 10, more preferably 1 to 6, and most preferably 1 to 4.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluene sulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flow ability and solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

"Substituted," as in substituted alkyl, means that the substitution can occur at one or more positions and, unless otherwise indicated, that the substituents at each substitution site are independently selected from the specified options, meaning that more than one substituent may be present simultaneously at various sites.

"Prodrugs" and "solvates" of the compounds of the invention are also contemplated herein. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield a compound of formula (I) or a metabolite, pharmaceutically acceptable salt or solvate of the compound. The transformation may occur by various mechanisms (e.g., by metabolic or chemical processes). A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

"Metabolites" of the compounds of the invention refer to the intermediates and products of metabolism.

The compounds of formula (I) may contain asymmetric or chiral centres, and, therefore, exist in different stereoisomeric forms. It is intended that all stereoisomeric forms of the compounds of formula (I) as well as mixtures thereof, including racemic mixtures, form part of the present invention. In addition, the present invention embraces all geometric and positional isomers. Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolysing) the individual diastereomers to the corresponding pure enantiomers. Enantiomers can also be separated by use of chiral HPLC column. The chiral centres of the present invention can have the S or R configuration as defined by the IUPAC 1974.

The use of the terms "salt", "solvate", or "prodrug" and the like, is intended to equally apply to the salt, solvate and prodrug of enantiomers, stereoisomers, rotamers, tautomers, positional isomers, racemates or prodrugs of the inventive compounds.

As used in this application, the singular form "a", "an" and "the" include plural references unless the context clearly dictates otherwise.

As used herein, the term "comprising" means "including." Variations of the word "comprising", such as "comprise" and "comprises," have correspondingly varied meanings. Thus, for example, a pharmaceutical composition "comprising" a compound of formula (I) may consist exclusively of that compound or may include one or more additional components (e.g. a pharmaceutically acceptable carrier, excipient and/or diluent).

As used herein the term "plurality" means more than one. In certain specific aspects or embodiments, a plurality may mean 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or more, and any integer derivable therein, and any range derivable therein.

"Therapeutically effective amount" means an amount of at least one compound of formula (I), or a metabolite, pharmaceutically acceptable salt, solvate or prodrug thereof, that substantially inhibits proliferation and/or prevents differentiation of a human tumor cell, including human tumor cell lines. The term "therapeutically effective amount" as used herein, includes within its meaning a non-toxic but sufficient amount of an agent or composition for use in the present invention to provide the desired therapeutic effect. The exact amount required will vary from subject to subject depending on factors such as the species being treated, the age and general condition of the subject, the severity of the condition being treated, the particular agent being administered, the mode of administration and so forth. Thus, it is not possible to specify an exact "effective amount" applicable to all embodiments. However, for any given case, an appropriate "effective amount" may be determined by one of ordinary skill in the art using only routine experimentation.

DETAILED DESCRIPTION

The AADs (e.g. formula (I)) are a class of compounds that may be synthesized using the ordinary knowledge of organic synthetic methodology. For example, the AADs may be synthesised by derivitisation of phenols with chloroacetone, Strecker reaction and acylation of the resultant amine with aroyl chlorides (as shown in Scheme 1). Where necessary, a particular enantiomer may then be obtained, for example, by chiral resolution (as shown in Scheme 2).

Scheme 1:

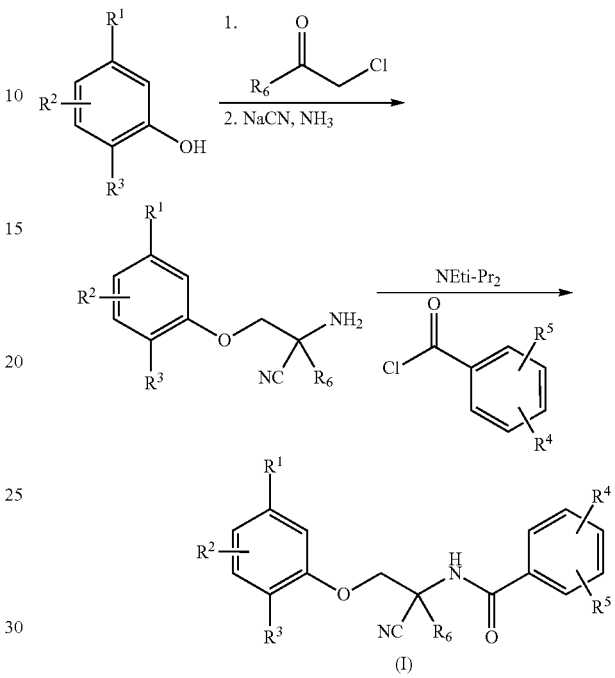

Scheme 2:

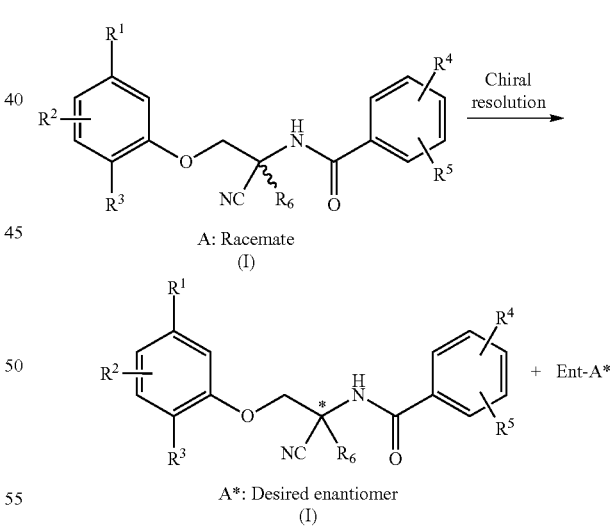

The AADs are a class of chemicals that have previously been used to treat drug-resistant nematodes. Research to date has focused on MPL targeting nicotinic acetyl choline receptors in nematodes, and has been used extensively for the treatment of parasites in ruminants.

mTOR (the mammalian Target Of Rapamycin), also known as mechanistic target of rapamycin or FK506 binding protein 12-rapamycin associated protein 1 (FRAP1), is a protein which in humans is encoded by the FRAP1 gene. mTOR is a serine/threonine protein kinase (and specifically belongs to the phosphatidylinositol 3-kinase-related kinase protein family) that regulates cell growth, cell proliferation, cell motility, cell survival, protein synthesis and transcription. mTOR is the catalytic subunit of the two molecular complexes mTORC1 and mTORC2. Despite the fact that MPL is rapamycin-like in interfering with the mTOR pathway, rapamycin is not typically an antihelminthic indicating MPL is very different to known mTOR inhibitors. Like rapamycin, however, AADs have both immunosuppressive qualities and anti-cancer activity.

The TOR family of proteins has pleiotropic functions, and participates in the regulation of the initiation of mRNA transcription and protein translation in response to intracellular concentrations of amino acids and other essential nutrients, in the organization of the actin cytoskeleton, membrane trafficking, protein degradation, PKC signalling and ribosome biogenesis. Furthermore, the mTOR pathway regulates many major cellular processes and is implicated in an increasing number of pathological conditions, including cancer, obesity, type 2 diabetes, and neurodegeneration.

There are two mTOR pathway containing complexes: a rapamycin-sensitive complex (mTORC1), which is defined by its interaction with the accessory protein Raptor (regulatory-associated protein of mTOR); and a rapamycin-insensitive complex (mTORC2), which is defined by its interaction with RICTOR (rapamycin-insensitive companion of mTOR). mTORC1 phosphorylates the well-characterized mTOR effectors S6 kinase 1 (S6K1, also known as p70S6K) and eukaryotic initiation factor 4E (eIF4E)-binding protein 1 (4EBP1, which is encoded by the gene phosphorylated heat- and acid-stable protein regulated insulin 1 (PHAS1)). mTORC2 controls the actin cytoskeleton as well as AKT/PKB.

mTOR regulates essential signal transduction pathways and is involved in coupling growth stimuli to cell cycle progression. In response to growth-inducing signals, quiescent cells increase the translation of a subset of mRNAs, the protein products of which are required for progression through the G1 phase of the cell cycle. PI3K and AKT are the key elements of the upstream pathway that links the ligation of growth factor receptors to the phosphorylation and activation state of mTOR. With regard to the role of the PI3K/AKT/mTOR pathway in the genesis and proliferation of cancer cells, elements of the PI3K/AKT/mTOR pathway have been demonstrated to be activated by the erythroblastic leukaemia viral oncogene homologue (ERB) family of surface receptors, the insulin-like growth factor receptors (IGFRs), and oncogenic Ras. Overexpression of insulin-like growth-factor 1 receptor (IGF1R) and its ligand, insulin growth-factor 1 (IGF1), commonly occurs in several cancers. Additionally, several elements of the PI3K/AKT/mTOR pathway have been demonstrated to be constitutionally activated in malignancies. The hyperactivation of PI3K/AKT/mTOR signalling elements in PTEN-deficient malignancies suggests that cancers often depend on this pathway for growth and sustenance.

Following phosphorylation, mTOR modulates two distinct downstream signaling pathways that control the translation of specific subsets of mRNAs including S6K1 and 4EBP1. Activation of either PI3K and/or AKT, and/or loss of PTEN suppressor function, is necessary and sufficient to induce the phosphorylation of both S6K1 and 4EBP1 through mTOR. Thus, rapamycin derivatives block the phosphorylation of S6K1 and 4EBP1 in cells expressing activated PI3K or AKT or lacking PTEN. The process by which mTOR transmits signals depends on its interaction with Raptor, an evolutionarily conserved protein of 150 kDa that forms a complex with mTOR and also binds to both 4EBP1 and S6K1. Although Raptor itself is not a kinase, it is required for the mTOR pathway mediated phosphorylation of 4EBP1 and S6K1.

4EBP1 is a small protein that represses the initiation of protein translation through its association with eIF4E, the mRNA cap-binding subunit of the eIF4F complex. Overexpression of eIF4E alone is sufficient to induce cell transformation. The binding of 4EBPs to eIF4E depends on the phosphorylation status of 4EBP1.

Regarding the interaction of mTOR with translation proteins, in quiescent cells and under growth-factor-deprived conditions, unphosphorylated 4EBP1 binds tightly to eIF4E, inhibiting initiation of protein translation. In response to proliferative stimuli triggered by hormones, growth factors, mitogens, cytokines and G-protein-coupled agonists, 4EBP1 becomes phosphorylated at several serine/threonine sites through the action of mTOR and other kinases, promoting the dissociation of eIF4E from 4EBP1. Free eIF4E can then bind to eIF4G (a large scaffolding protein), eIF4A (an ATP-dependent RNA helicase), and eIF4B, forming the multisubunit eIF4F complex and facilitating cap-dependent protein translation. This cascade of events induces an increase in translation of mRNAs with regulatory elements in the 5'-untranslated terminal regions (5'-UTR), including mRNAs that encode c-MYC, cyclin D1 and ornithine decarboxylase. By contrast, growth-factor deprivation or treatment with rapamycin results in dephosphorylation of 4EBP1, increased eIF4E binding and a concomitant impairment of the initiation of the translation of mRNAs with 5'-UTRs that is required for the G1-to-S phase transition of the cell cycle.

There is abundant experimental evidence indicating that mTOR is directly responsible for 4EBP1 phosphorylation and the activation of eIF4E induced by various mitogenic stimuli. For example, the phosphorylation of 4EBP1 in insulin-treated cells has been shown to be effectively blocked by mTOR inhibitors. In fact, a low cellular ratio of 4EBP1 to eIF4E can cause resistance to mTOR inhibitors. Furthermore, sites of 4EBP1 that are phosphorylated by mTOR are identical to those induced by insulin treatment, and are rapidly dephosphorylated following exposure to mTOR inhibitors. Some observations indicate that mTOR might also act indirectly as an inhibitor of a protein serine/threonine phosphatase, which functions to dephosphorylate 4EBP1 when conditions are appropriate for the G1-to-S phase transition.

There is substantial evidence which indicates that MPL binds to acetyl choline receptors in nematodes and lacks activity in mammalian cells. However as mentioned above, it has now been surprising been found that MPL selectively binds to mTOR receptors in mammalian cells.

The compounds of the present invention act as selective mTOR kinase inhibitors in mammalian cells by binding to mTOR receptors, and therefore may be used in the treatment of any mTOR pathway related disease.

Many cancer drugs, such as rapamycin and its analogs, bind to mTOR via a domain which is separate from the catalytic site and therefore block only a subset of mTOR functions. Such drugs could activate an mTOR pathway dependent survival pathway leading to treatment failure.

Figure 8:
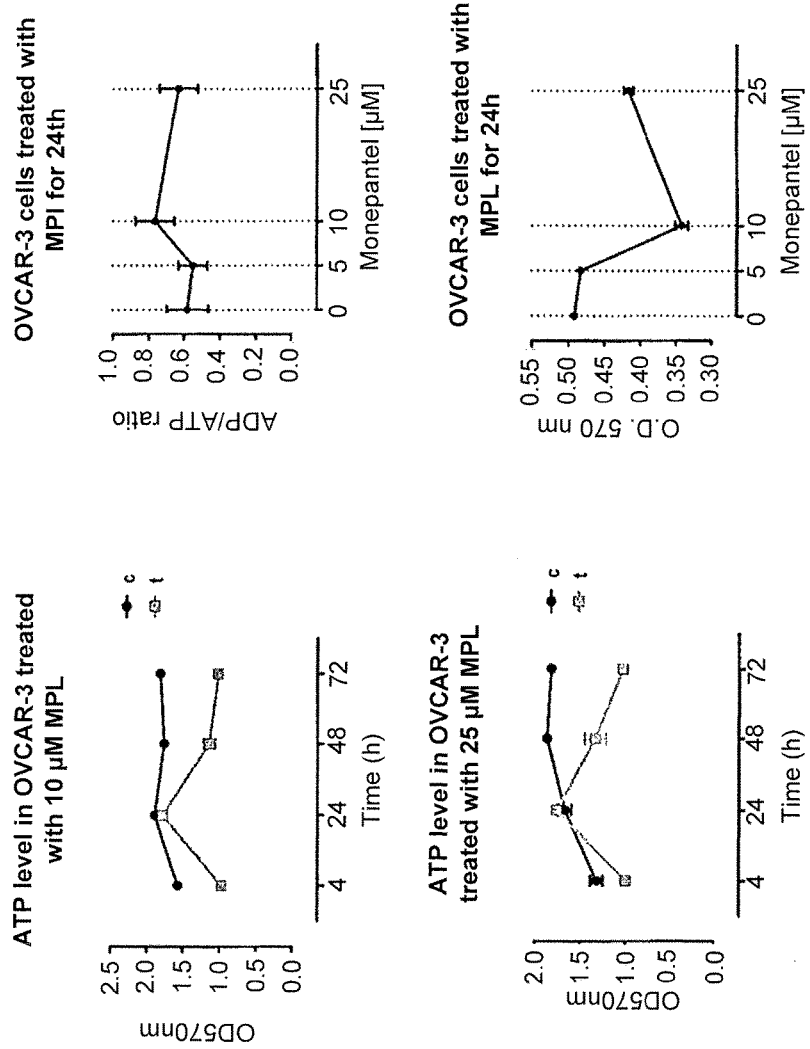
FIG. 8 shows the effect of MPL on ATP and the ADP/ATP ratio in the human ovarian cancer OVCAR-3 cell line. The exposure of cells to MPL under standard cell culture conditions leads to a reduction of ATP levels and consequently an increase in the ADP/ATP ratio. ADP and ATP levels in the media were measured using the commercial colorimetric/fluorometric assay kits from Abcam together with the Apo-Glow assay kit from Lonza (Sydney, Australia subsidary). Each value represents mean+s.e.m. of at least two determinations.

By contrast, the compounds of the present invention are of a similar size to ATP (adenosine triphosphate) and are therefore able to compete with ATP at the catalytic site of mTOR. Such interaction of the compounds of the present invention at the catalytic site of mTOR should inhibit all of the kinase-dependent functions of mTORC1 and mTORC2, and without risking the activation of a survival pathway. In FIG. 8, it is shown that MPL decreases ATP levels in ovarian cancer cells, which strongly indicates that MPL binds to the catalytic site of mTOR.

MPL appears to provide highly selective inhibition of mTOR, due to its low toxicity and, when used as an anthelmintic, its toleration by animals in doses up to 2000 mg/kg. In animal models the present inventors have shown that the anticancer effects of MPL are observed at surprisingly low doses of between 5-50 mg/kg.

mTOR signaling is often up-regulated in cancer. The interaction of MPL with mammalian mTOR receptors may be selective for tumour cells causing inhibition of tumour growth (see Australian Provisional Patent Application No. 2012901199 and PCT/AU2013/000290, which are incorporated herein by reference).

For example, the present inventors have surprisingly found that compounds of formula (I), such as MPL and MPL-SO$_2$, have anti-cancer activity. More specifically, compounds of formula (I), including MPL and MPL-SO$_2$, have been shown to inhibit cell proliferation and colony formation of cancer cell lines. For example, ovarian cancer cell lines have shown to be very sensitive to compounds of formula (I), and it is evident that other cell lines are also highly sensitive. These include breast cancer, mesothelioma, prostate cancer and glioblastoma cell lines. MPL is very effective against chemo-resistant, androgen insensitive PC-3 and DU 145 prostate cancer cells. Similarly, replication of PET and YOU cells (mesothelioma) and U87 cells (glioblastoma), which are also highly resistant to chemotherapy, are profoundly suppressed by MPL.

The present inventors have shown that MPL and its analogues have application in the following mTOR dependent diseases:

mTOR signaling intersects with Alzheimer's disease (AD) pathology in several aspects, suggesting its potential role as a contributor to disease progression. In general, findings demonstrate mTOR signaling hyperactivity in AD brains. For example, postmortem studies of human AD brain reveal dysregulation in PTEN, Akt, S6K, and mTOR;

Studies using mouse models of Huntington's disease demonstrate that treatment with rampamycin facilitates the clearance of huntington aggregates. MPL similarly can remove such aggregates providing a new treatments for this condition;

Age-related diseases;
Transplant rejection;
Chronic inflammatory diseases (e.g. rheumatoid arthritis);
Glycogen storage diseases;
Selective for certain cancers;
Systemic Lupus: mTOR signaling is increased in SLE T cells, and inhibition of mTOR signaling with rapamycin has been shown to be effective in the treatment of human SLE. SLE patients treated with rapamycin demonstrate lowered baseline calcium levels and decreased calcium influx following TCR stimulation, but do not show a change in mitochondrial function, indicating the specificity of rapamycin treatment on this manifestation of the disease;
Inflammation and immune activation;
Anaemia;
Leukopenia;
Thrombocytopenia;
Stent coating;
Renal insufficiency;
Obesity;
Diabetes/insulin resistance;
Non-alcoholic fatty liver;
Polycystic kidney;
Parkinson's Disease: the mTORC1 inhibitor rapamycin prevented the development of dyskinesia without affecting the therapeutic efficacy of L-DOPA. Thus, the mTORC1 signaling cascade represents a target for the design of anti-Parkinsonian therapies;
Fibrosis (such as liver, cardiac and pulmonary fibrosis). Due to the sensitivity of fibroblasts to MPL, the relation between PI3K/mTOR and TGFbeta, and the effect on lysyl oxidase (LOX) expression/activity, MPL may be used in the treatment of fibrosis. Increased cardiac LOX expression is found in patients with heart failure/fibrosis, and similarly a number of pulmonary and renal diseases/LOX/fibroblasts. Additionally, fibrosis is an important contributing factor in several types of cancers, such as breast and pancreatic cancer.

Without being bound by theory, it is believed that that activity of the compounds of the present invention act by binding to the catalytic site of mTOR.

Compositions, Medicaments and Kits

The present invention provides pharmaceutical compositions, medicaments and kits which comprise at least one compound of formula (I), or a metabolite, pharmaceutically acceptable salt, solvate or prodrug of said compound and at least one pharmaceutically acceptable carrier. For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions, for example water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen. Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably, the compound of formula (I) is administered orally.

Compositions and medicaments of the present invention may comprise a pharmaceutically acceptable carrier, adjuvant, excipient and/or diluent. The carriers, diluents, excipients and adjuvants must be "acceptable" in terms of being compatible with the other ingredients of the composition or medicament, and are generally not deleterious to the recipient thereof. Non-limiting examples of pharmaceutically acceptable carriers or diluents are demineralised or distilled water; saline solution; vegetable based oils such as peanut oil, safflower oil, olive oil, cottonseed oil, maize oil; sesame oils such as peanut oil, safflower oil, olive oil, cottonseed oil, maize oil, sesame oil, *arachis* oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxylpropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrolidone; agar; gum tragacanth or gum acacia, and petroleum jelly. Typically, the carrier or carriers will form from about 10% to about 99.9% by weight of the composition or medicament.

Composition and medicaments of the present invention may be in a form suitable for administration by injection (e.g. for parenteral administration including subcutaneous, intramuscular or intravenous injection), by oral administration (such as capsules, tablets, caplets, and elixirs, for example), by topical administration (e.g. in the form of an ointment, cream or lotion, or a form suitable for delivery as an eye drop), or by intranasal inhalation (e.g. in the form of aerosols).

For administration as an injectable solution or suspension, non-toxic parenterally acceptable diluents or carriers can include, Ringer's solution, isotonic saline, phosphate buffered saline, ethanol and 1,2 propylene glycol. Methods for preparing parenterally administrable compositions and medicaments are apparent to those of ordinary skill in the art, and are described in more detail in, for example, Remington's Pharmaceutical Science, 15th ed., Mack Publishing Company, Easton, Pa.

For oral administration, some examples of suitable carriers, diluents, excipients and adjuvants include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl stearate which delay disintegration. Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, *arachis* oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

Formulations for oral administration may comprise one or more emulsifying agents. Suitable emulsifying agents include dispersing agents as exemplified above or natural gums such as guar gum, gum acacia or gum tragacanth.

Topical formulations of the present invention may comprise an active ingredient together with one or more acceptable carriers, and optionally any other therapeutic ingredients. Formulations suitable for topical administration include liquid or semi-liquid preparations suitable for penetration through the skin to the site where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or *arachis* oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, *arachis*, castor or olive oil, wool fat or its derivatives, or a fatty acid such as stearic or oleic acid together with an alcohol such as propylene glycol or macrogols.

Compositions and medicaments of the present invention may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

Compositions and medicaments of the present invention may be administered in the form of a liposome. Suitable methods to form liposomes are known in the art, and in relation to this specific reference is made to Prescott, (Ed), (1976), "Methods in Cell Biology", Volume XIV, Academic Press, New York, N.Y. p. 33 et seq.

Supplementary active ingredients such as adjuvants or biological response modifiers can also be incorporated into compositions and medicaments of the present invention.

Any suitable adjuvant may be included in compositions and medicaments of the present invention. For example, an aluminium-based adjuvant may be utilised. Suitable aluminium-based adjuvants include, but are not limited to, aluminium hydroxide, aluminium phosphate and combinations thereof. Other specific examples of aluminium-based adjuvants that may be utilised are described in European Patent No. 1216053 and U.S. Pat. No. 6,372,223. Other suitable adjuvants include Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminium salts such as aluminium hydroxide gel (alum) or aluminium phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A; oil in water emulsions including those described in European Patent No. 0399843, U.S. Pat. No. 7,029,678 and PCT Publication No. WO 2007/006939; and/or additional cytokines, such as GM-CSF or interleukin-2, -7, or -12, granulocyte-macrophage colony-stimulating factor (GM-CSF), monophosphoryl lipid A (MPL), cholera toxin (CT) or its constituent subunit, heat labile enterotoxin (LT) or its constituent subunit, toll-like receptor ligand adjuvants such as lipopolysaccharide (LPS) and derivatives thereof (e.g. monophosphoryl lipid A and 3-Deacylated monophosphoryl lipid A), muramyl dipeptide (MDP) and F protein of Respiratory Syncytial Virus (RSV).

Another aspect of this invention is a kit comprising a therapeutically effective amount of at least one compound of formula (I), or a metabolite, pharmaceutically acceptable salt, solvate or prodrug of said compound and a pharmaceutically acceptable carrier, vehicle or diluent.

Another aspect of this invention is a kit comprising an amount of at least one compound of formula (I), or a metabolite, pharmaceutically acceptable salt, solvate or prodrug of said compound and an amount of at least one anticancer therapy and/or anti-cancer agent listed above, wherein the amounts of the two or more ingredients result in desired therapeutic effect.

Kits of the present invention may comprise components to assist in performing the methods of the present invention such as, for example, administration device(s), buffer(s), and/or diluent(s). The kits may include containers for housing the various components and instructions for using the kit components in the methods of the present invention.

In certain embodiments, the kits may be combined kits.

In other embodiments, the kits may be fragmented kits.

Dosages and Routes of Administration

The agents, compositions and medicaments can be administered to a recipient by standard routes, including, but not limited to, parenteral (e.g. intravenous, intraspinal, subcutaneous or intramuscular), oral, topical, or mucosal routes (e.g. intranasal). In some embodiments, they may be administered to a recipient in isolation or in combination with other additional therapeutic agent(s). In such embodiments the administration may be simultaneous or sequential.

In general, the agents, compositions and medicaments can be administered in a manner compatible with the route of administration and physical characteristics of the recipient (including health status) and in such a way that the desired effect(s) are induced (i.e. therapeutically effective, immunogenic and/or protective). For example, the appropriate dosage may depend on a variety of factors including, but not limited to, a subject's physical characteristics (e.g. age, weight, sex), whether the agent, composition or medicament is being used as single agent or adjuvant therapy, the progression (i.e. pathological state) of the cancer being treated, and other factors readily apparent to those of ordinary skill in the art.

Various general considerations when determining an appropriate dosage of the agents, compositions and medicaments are described, for example, in Gennaro et al. (Eds), (1990), "Remington's Pharmaceutical Sciences", Mack Publishing Co., Easton, Pa., USA; and Gilman et al., (Eds), (1990), "Goodman And Gilman's: The Pharmacological Bases of Therapeutics", Pergamon Press.

A surprising advantage of the present invention is that compounds of formula (I) generally reflect a low toxicity. For example, MPL has single-dose toxicity in excess of 2000 mg per kg of body weight. As such, an agent, composition or medicament for use in the present invention may be administered to a patient as a single dose of an amount of up to and including 2000 mg of active component(s) per kg of body weight. Moreover, another surprising advantage of using the present invention for the treatment of cancer is the generally high clinical tolerance of compounds of formula (I). For example, a dosage of 1000 mg of MPL per kg of body weight per 24 hours is well tolerated in mammals. As such, an agent, composition or medicament for use in the present invention may be administered to a patient in an amount of up to and including 1000 mg of active component (s) per kg of body weight per 24 hours.

Generally, an effective dosage is expected to be in the range of about 0.0001 mg to about 1000 mg of active component(s) per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; or about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; or about 5.0 mg to about 15 mg per kg body weight per 24 hours.

For example, a preferred dosage may be about 10-100 mg of the compound of formula (I) per kg of body weight per 24 hours. Further, a preferred dosage may be about 50 mg of a compound of formula (I) per kg of body weight per 24 hours.

Typically, in treatment applications, the treatment may be for the duration of the cancer. Further, it will be apparent to one of ordinary skill in the art that the optimal quantity and spacing of individual dosages can be determined by the nature and extent of the disease state or condition being treated, the form, route and site of administration, and the nature of the particular subject being treated. Optimum dosages can be determined using conventional techniques.

In many instances (e.g. preventative applications), it may be desirable to have several or multiple administrations of an agent, composition or medicament of the present invention which may, for example, be administered 1, 2, 3, 4, 5, 6, 7, 8, 9, 10, or more times. The administrations may be from about one to about twelve week intervals, and in certain embodiments from about one to about four week intervals. Periodic re-administration is also contemplated.

It will also be apparent to one of ordinary skill in the art that the optimal course of administration can be ascertained using conventional course of treatment determination tests.

Where two or more entities (e.g. agents or medicaments) are administered to a subject "in conjunction", they may be administered in a single composition at the same time, or in separate compositions at the same time, or in separate compositions separated in time.

Certain embodiments of the present invention involve administration of the agents, compositions or medicaments in multiple separate doses. Accordingly, the methods for prophylactic and therapeutic treatment described herein encompass the administration of multiple separated doses to a subject, for example, over a defined period of time. Accordingly, in some embodiments the methods include administering a priming dose, which may be followed by a booster dose. The booster may be for the purpose of re-vaccination. In various embodiments, the agent, composition or medicament is administered at least once, twice, three times or more.

The agents, compositions and medicaments may generally be administered in an effective amount to achieve an intended purpose. More specifically, they may be administered in a therapeutically effective amount which means an amount effective to prevent development of, or to alleviate the existing symptoms of, a target disease or condition. Determination of effective amounts is well within the capability of persons of ordinary skill in the art. For example, a therapeutically effective dose of the agents, compositions and medicaments can be estimated initially from cell culture assays. For example, a dose can be formulated in animal models to achieve a circulating concentration range that includes the IC50 as determined in cell culture. Such information can be used to more accurately determine useful doses in humans and other mammalian subjects.

A therapeutically effective dose refers to that amount of the agent, composition or medicament to prevent development of symptoms, ameliorate symptoms and/or prolong the survival of the subject under treatment. Toxicity and therapeutic efficacy of the agents, compositions and medicaments can be determined by standard pharmaceutical assays in cell cultures, and/or experimental animals (e.g. by determination of the LD50 (the dose lethal to 50% of the population) and the ED50 (the dose therapeutically effective in 50% of the population)). The dose ratio between toxic and therapeutic effects is the therapeutic index which can be expressed as the ratio between LD50 and ED50. Agents, compositions and medicaments which exhibit high therapeutic indices are preferred. The data obtained from such cell culture assays and/or animal studies may be used to formulate a range of dosage for use in humans or other mammals. The dosage of such compounds lies preferably within a range of circulating concentrations that include the ED50 with little or no toxicity. The dosage may vary within this range depending upon the dosage form employed and the administration route utilised. The exact formulation, route of administration and dosage can be selected without difficulty by an individual physician in view of the subject's condition (see, for example, Fingl et al., (1975), in "The Pharmacological Basis of Therapeutics", Ch. 1 p. 1). Dosage amount and interval may be adjusted individually to provide plasma levels of the active agent sufficient to achieve and maintain the desired therapeutic effect/s and/or a minimal effective concentration (MEC). Dosages necessary to achieve the MEC will depend on the route of administration and other individual characteristics. Bioassays and/or HPLC assays may be used to determine plasma concentrations.

Dosage intervals may also be determined using MEC value. In general, the agents, compositions and medicaments may be administered using a regimen which maintains plasma levels above the MEC for between about 10%-90% of the time, preferably between 30%-90% and more preferably between about 50%-90%. In embodiments where local administration or selective uptake is utilised, the effective local concentration of the drug may not be related to plasma concentration.

The compounds of this invention may also be useful in combination (administered together or sequentially) with one or more of anti-cancer treatments such as radiation therapy, and/or one or more anti-cancer agents selected from the group consisting of cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™ (4-[2-[4-[(11R)-3,10-dibromo-8-chloro-6,11-dihydro-5H-benzo[5,6] cyclohepta[1,2-b]pyridin-11-yl-]-1-piperidinyl]-2-oxoethyl]-1-piperidinecarboxamide, or SCH 66336 from Schering-Plough Corporation, Kenilworth, N.J.), tipifarnib (Zamestra® or R115777 from Janssen Pharmaceuticals), L778.123 (a famesyl protein transferase inhibitor from Merck & Company, Whitehouse Station, N.J.), BMS 214662 (a famesyl protein transferase inhibitor from Bristol-Myers Squibb Pharmaceuticals, Princeton, N.J.); signal transduction inhibitors (such as, lressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-lntron (from Schering-Plough Corporation); hormonal therapy combinations; aromatase combinations; ara-C, adriamycin, Cytoxan, and gemcitabine.

Subjects

Prophylactic and therapeutic methods of the present invention may be applied to any suitable subject. In some embodiments, the subject is a mammalian subject. For example, the subject may be a mouse, rat, dog, cat, cow, sheep, horse or any other mammal of social, economic or research importance. Hence, the subject may be a mammal such as, for example, a human or a non-human mammal.

It will be appreciated by persons of ordinary skill in the art that numerous variations and/or modifications can be made to the present invention as disclosed in the specific embodiments without departing from the spirit or scope of the present invention as broadly described. The present embodiments are, therefore, to be considered in all respects as illustrative and not restrictive.

The present invention will now be described with reference to specific examples, which should not be construed as in any way limiting.

Examples

Materials and Methods

Cell Lines

The human ovarian cancer cell lines OVCAR-3, SKOV-3 and A2780 and primary cells human umbilical vein endothelial cells (HUVEC) and all other cell lines were obtained from the American Type Culture Collection (ATCC) and maintained according to their instructions. Astrocytes and glioma cell lines were kindly gifted by Dr. Kerry McDonald from Lowy Cancer Research Centre, University of New South Wales, Australia. Astrocytes and glioma cell lines were kindly gifted by Dr. Kerry McDonald from Lowy Cancer Research Centre, University of New South Wales, Australia.

Cell Proliferation Assay

Cell proliferation was assessed using the sulforhodamine B (SRB) assay. Cells seeded in 96-well plate (2,000-3,000 cell/well) were treated with MPL (0, 1, 5, 10, 25, 50 and 100 µmol/L) for 72 h. Cells were then fixed, washed and stained with 100 µl of 0.4% (w/v) SRB dissolved in 1% acetic acid. Unbound dye was removed by five washes with 1% acetic acid before air drying. Bound SRB was solubilized with 100 µl of 10 mM Tris base (pH 10.5) and the absorbance read at 570 nm. Exactly the same procedure was used to assess MPL-$SO_2$. Both agents were dissolved in ethanol and diluted with media to give the final concentrations required for cell culture assays.

Cell Viability Assay

For viability experiments, cells seeded in 6 well plates were exposed to monepantel (MPL) at 0, 1, 10, 50 and 100 µM concentrations for 24, 48 or 72 h. Monepantel (gift by Novartis, Basel, Switzerland) was dissolved in 100% ethanol and then diluted with the cell culture media. At the end of treatment period, cells were washed with PBS, trypsinized and counted using Trypan blue and hemocytometer. All experimental points were set up in quadruplicate and each experiment was performed at least twice.

Colony Formation Assay

For colony formation assay, $5 \times 10^6$ cells, such as OVCAR-3 or A2780 cells, were plated in 100 mm Petri dishes and allowed to attach overnight. Media were aspirated off and exponentially growing cells were incubated with various concentrations of MPL for 72 h. At this point, the medium was aspirated, the dishes were washed with PBS, and drug free medium was added to each plate. Media were changed twice weekly for 3 weeks. Following this, plates were gently washed with PBS and cells were fixed with 100% ethanol and stained with a 0.5% solution of filtered crystal violet. Colonies consisting of more than 50 cells were counted under an inverted microscope.

Cell Cycle Analysis

The effect of MPL on the cell cycle was determined using standard flow cytometry analysis protocols and procedures. Briefly, $0.7 \times 106$ million cells seeded in 25 cm3 flasks and allowed to adhere overnight were treated with MPL for 24 or 48 h. Cells were collected with trypsinization and pooled with the cells floating in the medium. The cell suspensions were centrifuged, washed with PBS and fixed with methanol. Cells were then washed, resuspended in propodium iodide and ribonuclease A in PBS for 30 min at room temperature and analyzed by flow cytometry (Becton Dickinson FACSort).

Western Blot Analysis

Protein expression in cells was determined using western blot analysis. After treatment with the indicated concentrations of MPL, cell lysates were prepared and probed with antibodies for cdk2, cdk4, cyclin A, cyclin E, PARP-1 (1:1000 dilutions; Cell Signalling Technology), and p53 (1:200 dilutions; Santa Cruz Biotechnology). Comparable loading of proteins on the gel was verified by re-probing the blots with a GAPDH antibody (1:30000 dilutions; Sigma-Aldrich).

In further experiments, after treatment with the indicated concentrations of MPL, cell lysates were prepared and probed with antibodies for c-Myc, cyclin D1, cyclin E, cdk2, cdk4, IGF-1R (Cell Signalling Technology), and (anta Cruz Biotechnology, Australia). Comparable loading of proteins on the gel was verified by re-probing the blots with a GAPDH antibody (Sigma-Aldrich, Sydney, Australia).

In Vivo Experiments

Female nude mice (6 weeks old) were purchased from Biological Resources (Faculty of Medicine, University of New South Wales). An institutional animal ethics approval covered all procedures carried out on mice. Briefly, $2.5 \times 106$ log-phase growing OVCAR-3 cells were injected s.c. into the left flank of each mouse. Animals were weighed once weekly while their tumor volumes were determined twice weekly. Tumor growth was monitored by caliper measurements of orthogonal diameters, and the estimated tumor volume was calculated based on the formula ½ (Length× Width$^2$), where width is the shorter of the two orthogonal measurements. Based on institutional ethics approval, mice were euthanized before the tumor volume reached 500 mm$^3$. Treatment was initiated on day 8 after tumor cell injection when mice were randomized and assigned to treatment or the control group (6 per group). Monepantel was suspended in sterile 0.5% (w/v) hydroperoxymethyl cellulose (HPMC). Drug was administered i.p. 3 times weekly at 25 or 50 mg/kg. Control group was treated with sterile vehicle (0.5% HPMC). Mice were treated for a period of 3 weeks. Twenty four hours post-last drug administration, mice were euthanized and their tumors excised and frozen at −80° C. until analysis.

In alternative experiments, treatment was initiated on day 8 post tumor cell inoculation when mice were randomized and assigned to one of MPL or vehicle treated groups (5-6 mice per group). MPL was suspended in hydroperoxy methylcellulose (0.5% w/v HPMC), sterilized by sonnicator and administered every other day either intraperitoneally (i.p) or orally as gavage (100 μL). In the first pilot trial, the drug was administered i.p. at 2.5 or 25 mg/kg body weight, three times weekly for 2 weeks. Following the outcome, in the next set of animals, the dose was increased to 25 and 50 mg/kg, three times weekly. In the last (third) pilot study, mice were treated orally. The doses administered were 50 and 100 mg/kg three times weekly. In all these trials, mice in control groups received similar volume of the vehicle (0.5% HPMC). Tumor histology/immunohistochemistry was performed on formalin fixed tumor slices according to standard procedures.

Statistical Analysis

All data are reported as the mean±standard errors (S.E.M.) from at least two independent experiments. Differences in tumor volume between MPL treated versus control group were analysed using one way ANOVA with post hoc Dunnett test. Quantitative variables were compared using the Student's t test. Significant statistical difference was defined at $P<0.05$.

Results

MPL Inhibits Cell Proliferation

The effect of MPL was examined on the growth of ovarian cancer cell lines of OVCAR-3, A2780 and SKOV-3. By employing the SRB assay, the effect of MPL on cell proliferation was examined. MPL inhibited proliferation of OVCAR-3, A2780 and SKOV-3 cells in a concentration-dependent manner with IC50 values of 6.3, 10.0 and 29.3 respectively, according to Table 1. It is evident from these results that ovarian cancer cell lines are sensitive to the anti-proliferative effects of MPL. SKOV-3 cells were the least sensitive. MPL-SO$_2$ was also tested in a similar manner using the SRB proliferation assay. It was found that MPL-SO$_2$ is as potent as MPL. MPL-SO$_2$ reduced viability of cancer cell-lines growing in culture and inhibited cell proliferation. IC50 values for MPL-SO$_2$ are presented in Table 1.

The inhibitory effect of MPL on cell proliferation was also tested on a range of cells, such as breast, prostate and mesothelioma cells. Results obtained are presented in Table 1. Further results are presented in Table 2.

TABLE 1

IC50 values for MPL and MPL-SO$_2$ (72 h in vitro treatment, SRB assay)

| Cell Lines | Type of cancer | IC50 (μM) MPL | MPL-SO$_2$ |
|---|---|---|---|
| OVCAR-3 | Ovarian cancer | 6.3 | 5.5 |
| A2780 | Ovarian cancer | 10.0 | 4.2 |
| SKOV-3 | Ovarian cancer | 29.3 | 26 |
| IGROV-1 | Ovarian cancer | 6.1 | — |
| 1A9 | Ovarian cancer | 1.8 | 4.8 |
| T47-D | Breast cancer | 5.7 | — |
| MDA-MB-231 | Breast cancer | 24.0 | 23.6 |
| MCF-7 | Breast cancer | — | 7.3 |
| PET | Mesothelioma | 26.3 | — |
| YOU | Mesothelioma | 23.1 | — |
| PC-3 | Prostate cancer | 21.6 | — |
| DU-145 | Prostate Cancer | 23.5 | — |
| U87 | Glioblastoma | 26.2 | 20.5 |
| HUVEC | Human Umbilical Vein Endothelial Cells | 87.8 | 47.8 |
| CHO | Chinese Hamster Ovary | — | 73.7 |
| HEK | Human Embryonic Kidney | 50.5 | — |

TABLE 2

IC50 values for MPL and MPL-SO2 in suppressing proliferation of various cancer cell lines.

| Cell Line | Cell Type | IC$_{50}$ (μM) MPL | MPL-SO2 |
|---|---|---|---|
| OVCAR-3 | Ovarian Cancer | 6.3 ± 0.8 *** | 5.5 ± 1.3 *** |
| A2780 | Ovarian Cancer | 10 ± 3.8 ** | 4.2 ± 2.1 ** |
| SKOV-3 | Ovarian Cancer | 31.18 ± 0.76*** | 26 |
| IGROV-1 | Ovarian Cancer | 4.4 ± 0.27** | 4.4 ± 1.5** |
| 1A9 | Ovarian Cancer | 2.5 ± 0.45** | 3.42 ± 0.1** |
| T47-D | Breast Cancer | 5.3 ± 0.003** | 10.2 ± 0.6** |
| MDA-MB-231 | Breast Cancer | 23.8 ± 0.2** | 21.6 ± 7.5 *** |
| MCF-7 | Breast Cancer | 15.4 ± 1.1** | 8.0 ± 0.7** |
| PET | Mesothelioma | 26 | — |
| YOU | Mesothelioma | 23 | — |
| PC-3 | Prostate Cancer | 21 | — |
| DU-145 | Prostate Cancer | 23 | — |
| SW-876 | Liposarcoma | 14.57 | — |
| HT-1080 | Fibrosarcoma | 17.16 | — |
| U87 | Glioma | 18 ± 7.1** | 20.5 ± 1.0 ** |
| LN-18 | Glioma | 9.38 ± 0.79** | 6.64 ± 0.71** |
| T98G | Glioma | 18.2 ± 0.61 | 25.4 ± 0.28** |
| U251 | Glioma | 17 ± 1.2** | — |
| HCT-116 | Colorectal Cancer | 10.5 ± 0.02** | 22.5 ± 5.7** |
| HT-29 | Colorectal Cancer | 5.86 ± 0.2** | 2.75 ± 0.7** |
| HT-29 5m11 | Colorectal Cancer | 10.4 | 21.7 |
| HeLa | Epithelial (Adenocarcinoma) | 15.8 ± 0.3** | 18.2 ± 2.6** |
| HUVEC | Human Umbilical Vein Endothelial Cells | 87 | 47 |
| CHO | Chinese Hamster Ovary | 34.61 ± 0.789*** | 73.7 ± 6.0 ** |
| HEK | Human Embryonic Kidney | 34.57 ± 0.86** | — |
| 3T3 | Fibroblast | 12.41 ± 0.37** | 11.2 ± 1.1** |
| HaCat | Keratinocyte | 21.2 ± 3.2** | 42.68 ± 8.0** |
| Human Fetus Astrocytes | Astrocytes | 85.55 ± 2.7** | — |

No star = one determination,
**= two repetitions,
***= three repetitions

TABLE 3

| AAD | AHC # | MW | Formula | IC50 μM OVCAR-3 | IC50 μM A2780 | IC50 μM CHO | IC50 μM HUVEC |
|---|---|---|---|---|---|---|---|
| 1 | 450 | 0942648 | 382.77 | C18H14ClF3N2O2 | 23.85 ± 1.45 | 33.5 ± 8.5 | 45.87 | 96.5 |
| 2 | 907 | 2000020 | 416.32 | C19H14N2O2F6 | 18.9 ± 4.1 | 27.65 ± 7.15 | 169 | 55.18 |
| 3 | 970 | 2000114 | 432.37 | C19H14N2O3F6 | >100 | >100 | 142 | 139.8 |
| 4 | 1154 | 2001354 | 433.21 | C18H13N2O3F3Cl2 | 20.5 ± 0.5 | 28.0 ± 4.5 | 34.8 | 61.1 |
| 5 | 1336 | 2017686 | 479.20 | C18H12N2O3F5Br | 14.65 ± 1.25 | 17.0 ± 1.2 | 31.8 | 61.3 |
| 6 | 1470 | 2033757 | 468.30 | C19H12N2O3F8 | 12.9 ± 0.3 | 19.5 ± 4.1 | 32.2 | 74.0 |
| 7 | 004 | 2060021 | 416.75 | C18H13N2O3F4Cl | 18.58 ± 2.4 | 27.3 ± 0.5 | 57.3 | 93.0 |
| 8 | 2009 | 2062412 | 416.75 | C18H13N2O3F4Cl | 34.3 ± 4.3 | 75.9 ± 1.9 | 198 | 129.9 |
| MPL-(S) | 1566 | 2082782 | 473.39 | C20H13N3O2F6S | 7.9 ± 0.9 | 11.3 ± 0.9 | 34.61 | 65.0 |
| MPL-(R) | 2224 | 2102224 | 473.39 | C20H13N3O2F6S | 8.0 ± 0.7 | 14.75 ± 0.45 | 23.4 | 108.8 |

OVCAR-3, A2780 are human epithelial ovarian cancer;
CHO = Chinese hamster ovarian cells;
HUVEC = human umbilical vein endothelial cells

TABLE 4

Amino-acetonitrile derivatives (AADs) according to Table 3

AAD

| AAD | R1 | R2 | R3 | R4 |
|---|---|---|---|---|
| 1566 (MPL) | CN | H | $CF_3$ | $SCF_3$ |
| 2105 (MPL-SO) | CN | H | $CF_3$ | $SOCF_3$ |
| 4670 (MPL-SO$_2$) | CN | H | $CF_3$ | $SO_2CF_3$ |
| 450 | H | H | Cl | $CF_3$ |
| 907 | H | H | $CF_3$ | $CF_3$ |
| 970 | H | H | $CF_3$ | $OCF_3$ |
| 1154 | Cl | H | Cl | $OCF_3$ |
| 004 | F | H | Cl | $OCF_3$ |
| 2009 | H | F | Cl | $OCF_3$ |
| 1336 | F | F | Br | $OCF_3$ |
| 1470 | F | F | $CF_3$ | $OCF_3$ |

According to Table 3, "MPL-(R)" refers to N-[(1R)-1-cyano-2-(5-cyano-2-trifluoromethyl-phenoxy)-1-methyl-ethyl]-4-trifluoromethylsulfanyl-benzamide, and "MPL-(S)" refers to N-[(1S)-1-cyano-2-(5-cyano-2-trifluoromethyl-phenoxy)-1-methyl-ethyl]-4-trifluoromethylsulfanyl-benzamide.

According to the results shown in Table 3, the ratio of IC50 values (normal cell/cancer cell) for AADs 907, 1336, 1470 and 2224 (MPL-(R)) show particularly high activity. Further, AADs 2224 (MPL-(R)) and AAD 1566 (MPL-(S)) were found to be equipotent. It is noted that the (R)-enantiomer MPL-(R) has previously been shown to have no anthelmintic activity.

Figures 9A, 9B:
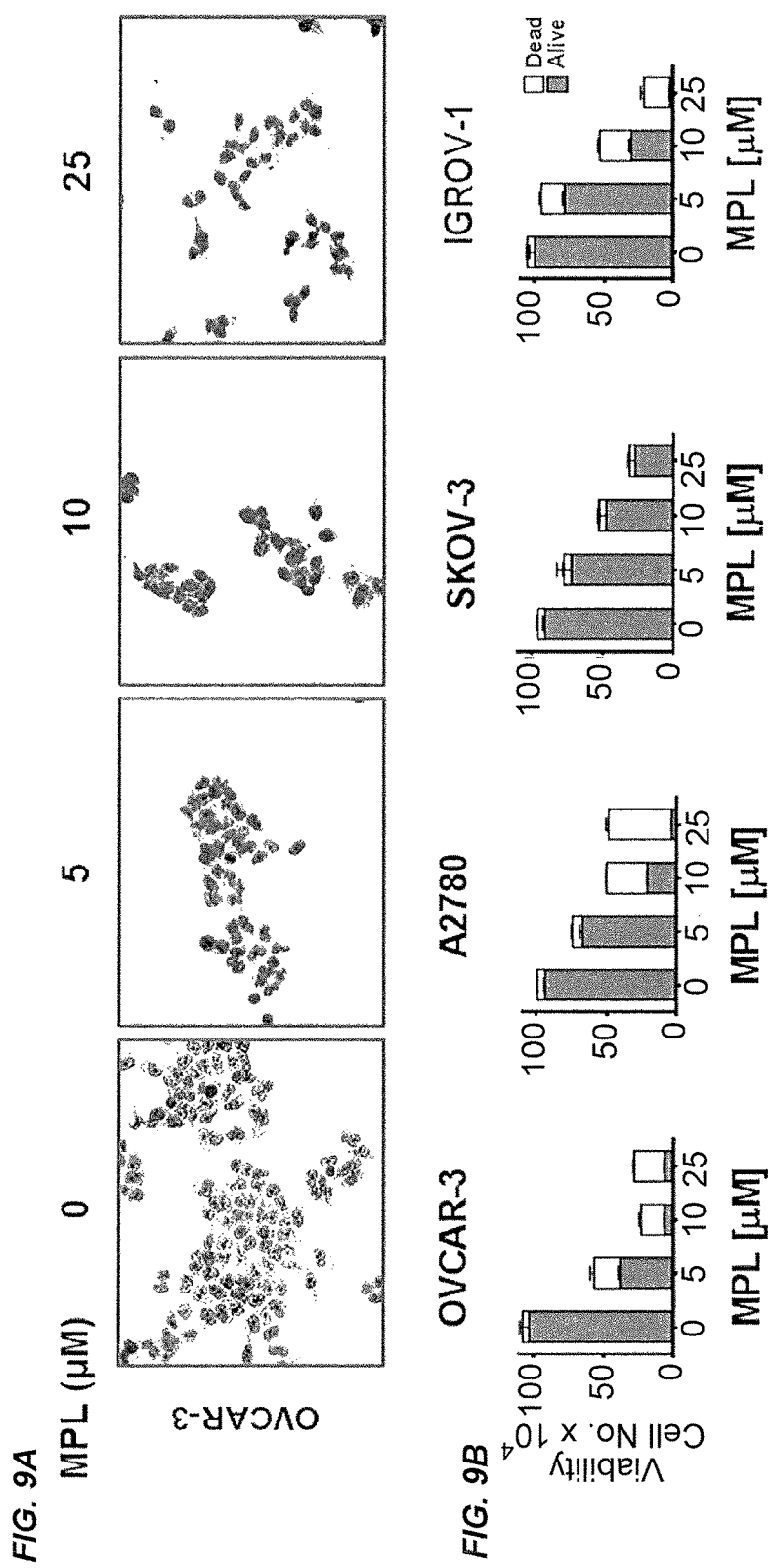
FIG. 9A and FIG. 9B show MPL interference with cell viability.
Figure 11:
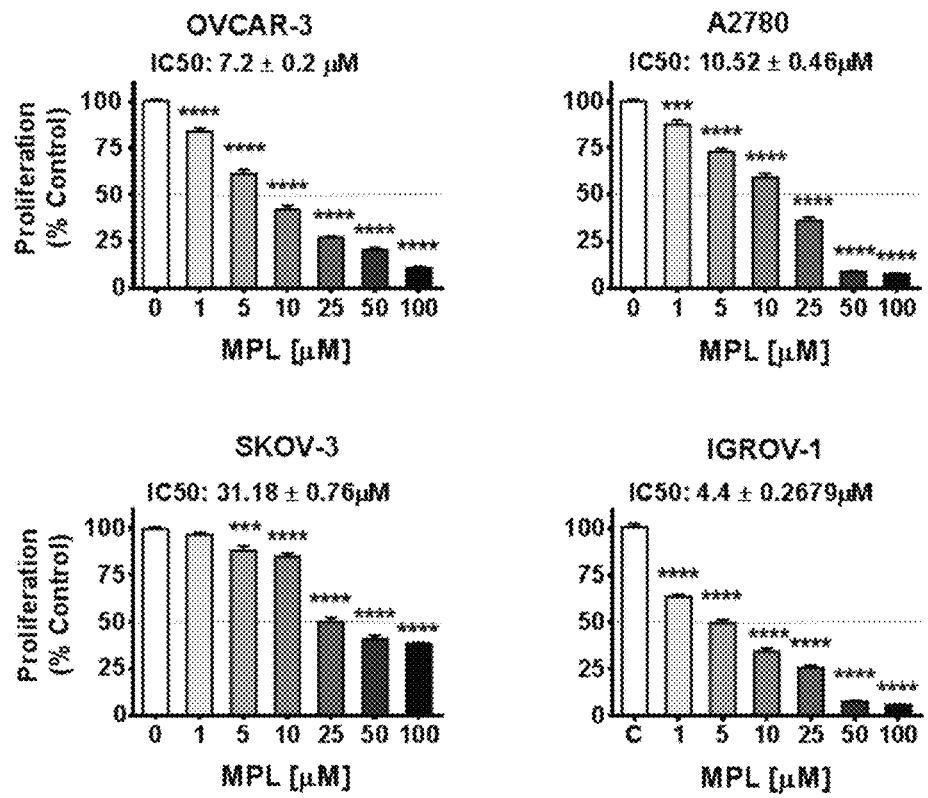
FIG. 11 shows how MPL inhibits cell proliferation. Human ovarian cancer cell lines OVCAR-3, A2780 and SKOV-3 and IGROV-1 were all cultured in the presence of MPL (0, 5, 10, 25, 50 and 100 µmol/L) for 72 h. Effect of MPL on cell proliferation was assessed using the SRB assay. Control (vehicle treated) cells were taken to present 100% proliferation and the MPL treated groups are expressed as percentage of control. Each drug concentration was tested in quadruplicate and each experiment was repeated at least twice. The data (mean±SEM) are presented as % control. For statistical comparisons, each drug treated group was compared with the control group using Student's t test. (A): Atropine: muscarinic Ach. receptor antagonist, Tobucorarine: nicortinic Ach. receptor antagonist, Mecamylamine: nonselective, noncompetitive nicotinic receptor antagonist; (B): Carbachol: muscarinic nicotinic ach. receptor agonist, Nicotine: Nicotinic ach. receptor agonist, Alpha-bungarotoxin: selective α7, nicotinic ach receptor agonist.
Figure 13:
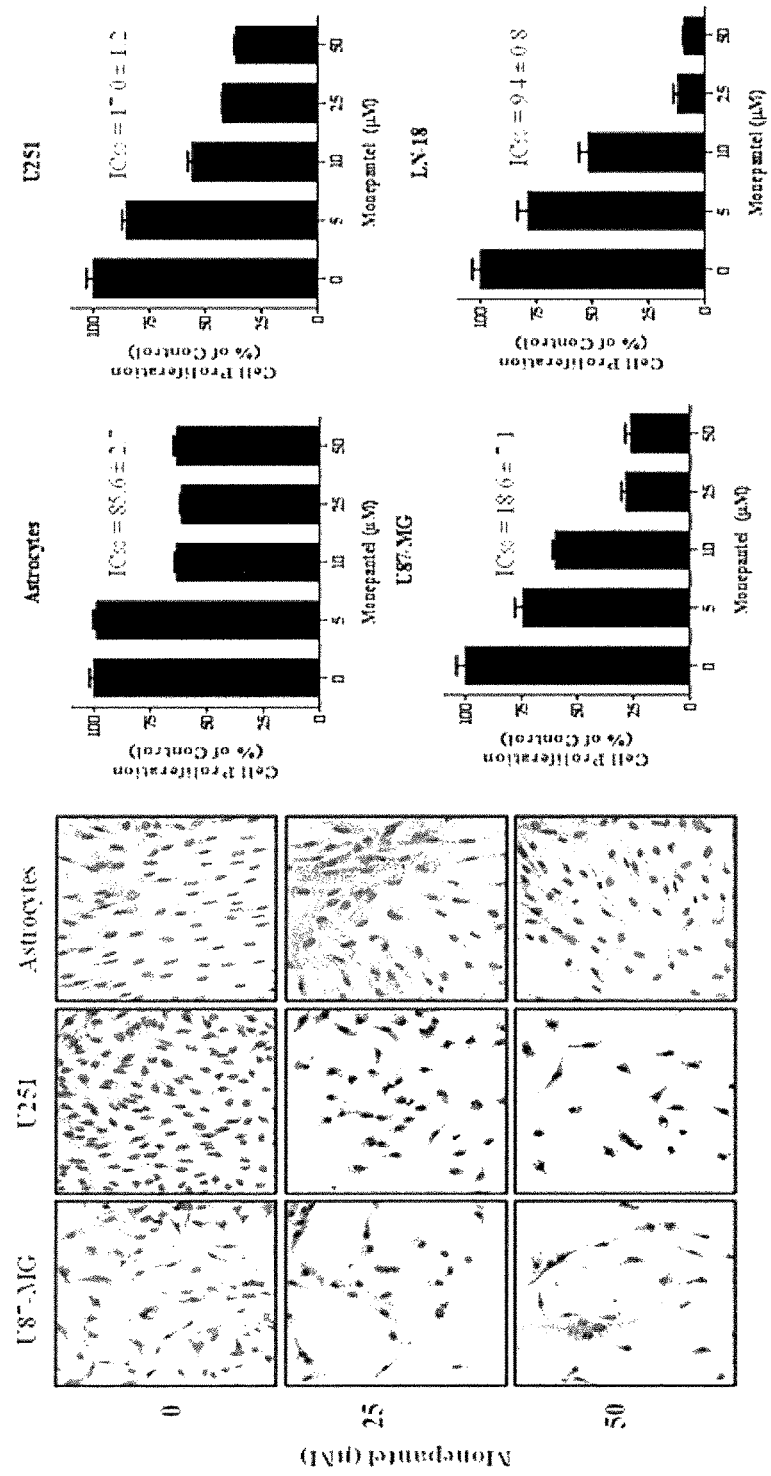
FIG. 13 shows how MPL inhibits proliferation of glioma cells. Comparison of the effect of MPL treatment (0, 5, 10, 25, 50 µM; 72 h) on the proliferation of U87-MG, U251 glioma cell lines versus normal astrocytes under normal cell culture conditions and using SRB proliferation assay. Data are presented as % control.
Figure 14:
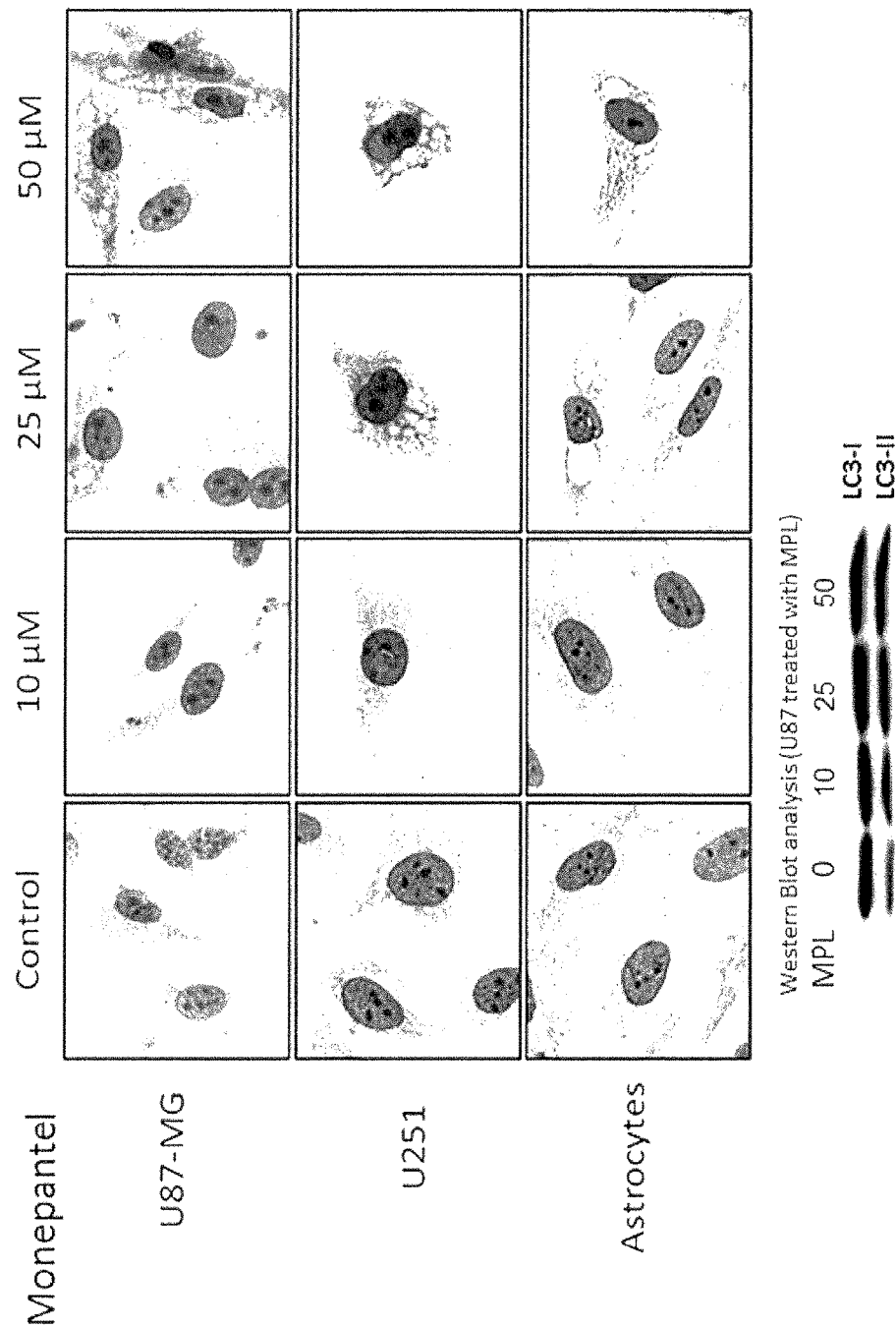
FIG. 14 shows how MPL induces autophagy. The treatment of chemo-resistant U87 glioma cells with MPL leads to autophagy, which is confirmed by increased expression of LC3-II in a concentration-dependent manner. U87-MG and U251 glioma cells treated with MPL demonstrated concentration-dependent formation of autophagy (shown as vacuoles). Concentration-dependent conversion of LC3-I to LC3-II confirms the increasing phenomenon of autophagy in these cells.

In brief, MPL and MPL-SO2 were tested in vitro against a wide range of cancer cell-lines with extensively different disease characteristics. For further detailed studies, human ovarian cancer cell lines OVCAR-3 and A2780 were chosen. Additionally, normal human ovarian surface epithelial cells (HOSE) and were cultured in the presence of MPL (0, 5, 10, 25, 50 and 100 μM) for 72 h. Cell viability was assessed using Trypan blue assay (FIG. 9). Similarly, effect of MPL on the growth of normal epithelial, endothelial, embryonic and fetal cells were investigated (FIG. 10) while cell proliferation was assessed using the SRB assay (FIG. 11). Control (vehicle treated) cells were taken to present 100% proliferation and the MPL treated groups are expressed as percentage of control±SEM. Each drug concentration was tested in quadruplicate and each experiment was repeated at least twice. For statistical comparisons, each drug treated group is compared to the control group using Student's t test. To examine concentration dependent drug effect, analysis of variance (ANOVA) was used. P values are: *=<0.05; <0.01 and *=<0.001, **** p<0.0001. Results presented in Table 2 reveal that MPL exerts high antiproliferative activity in cancer cell lines, whereas, normal cells are far less affected. In order to find out if the MPL effect is mediated through the nicotinic acetyl choline receptor and in particular the nACHR7 subtype, cells were pretreated with antagonists and then exposed to MPL (FIG. 12).

Results obtained for MPL-SO2 are also presented. It can be seen that MPL-SO2 acts in a similar order as the parent drug MPL. The range of IC50 values are very close and suggest that MPL-SO2 is as effective as MPL in suppressing cancer cell proliferation (Table 2).

MPL Inhibits Colony Formation

To investigate whether MPL also hinders the reproductive integrity and the ability of cell lines to establish colonies, the clonogenic activity of cells exposed to MPL was investigated. Following 72 h exposure to various concentrations of MPL, cells were washed and then incubated in drug free media for 2 weeks. It was found that MPL profoundly hinders colony formation by these cells. Higher concentrations of MPL led to almost complete loss of clonogenic ability (FIG. 2).

Figure 15:
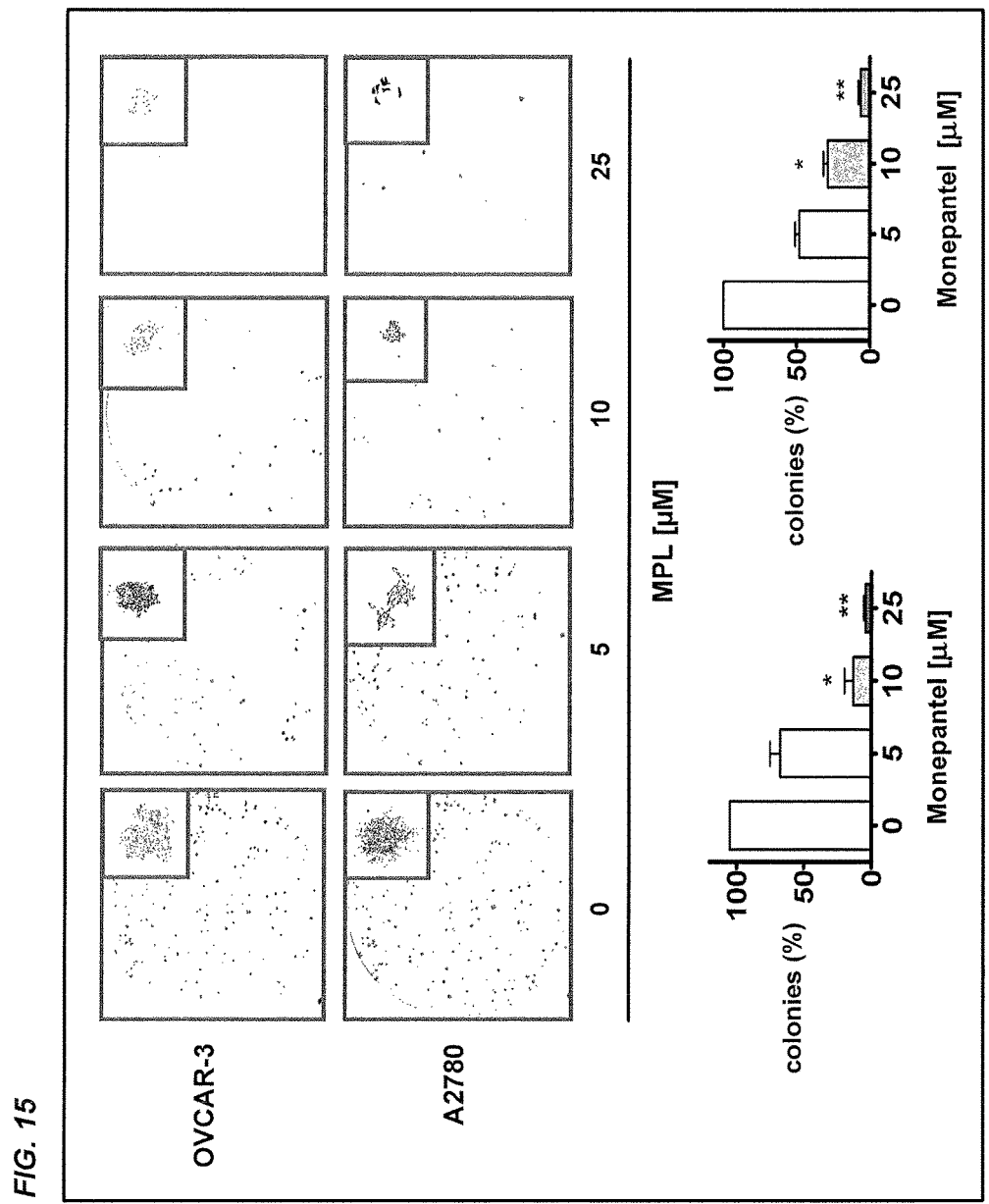
FIG. 15 shows the effect of MPL on the colony formation activity of OVCAR-3 and A2780 cells. Following incubation of cells with MPL (0, 5, 10, 25 µM) for 72 h, cells were washed and then transferred to agar plates, cultured with their regular growth medium and incubated under standard conditions for 2 weeks. Cells were then fixed with 100% methanol and stained with 1% crystal violet. Colonies (cluster of cells greater than 50) were counted under microscope (magnification ×5). Number of colonies counted for different experimental groups is expressed as % of control.

To determine the effect of MPL on cell integrity and capacity to rid itself from drug effects following drug exposure and withdrawal, cells were incubated with MPL (0, 5, 10, 25 μM) for 72 h, washed with PBS, transferred to agar plates, cultured with growth medium and incubated under standard conditions for 2 weeks. Cells were then fixed with 100% methanol and stained with 1% crystal violet. Colonies (Cluster of cells greater than 50) were counted under microscope (magnification ×5). Number of colonies counted for different experimental groups is expressed as percentage of the control (FIG. 15). These results demonstrate concentration-dependent inhibition of colony formation by MPL.

Figure 3A:
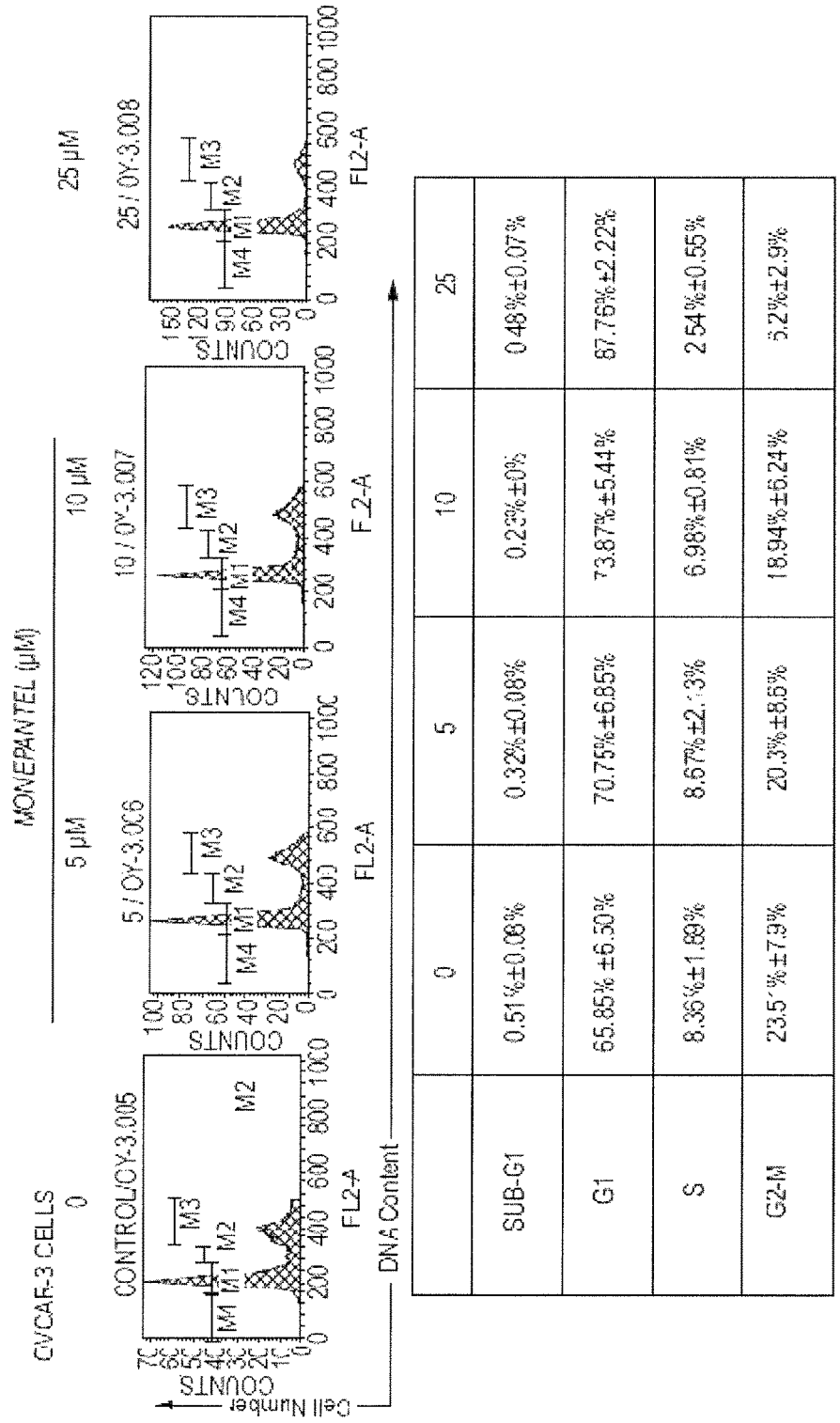
FIG. 3A shows how MPL interferes with the cell cycle distribution of OVCAR-3 cells.
Figure 3B:
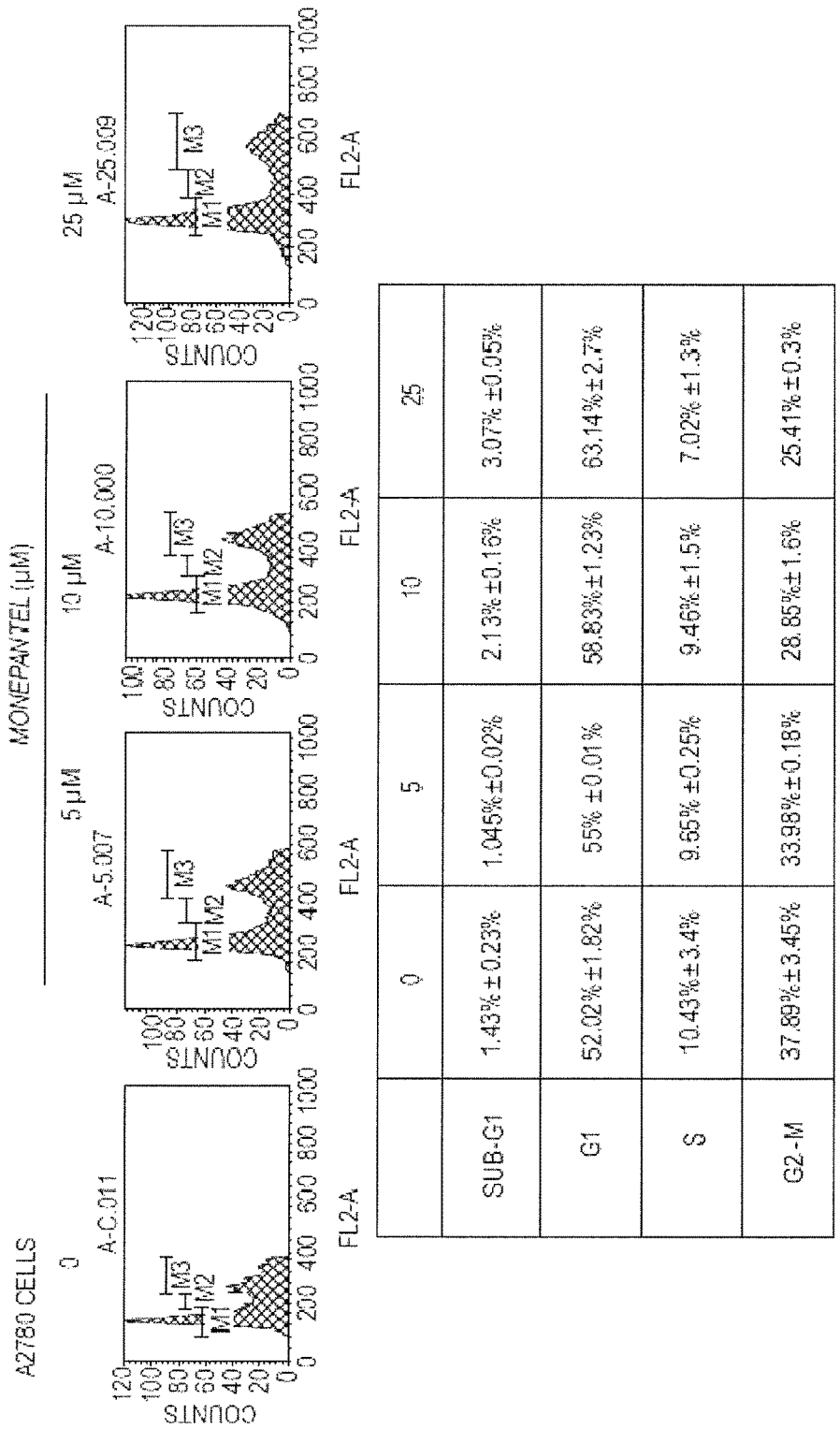
FIG. 3B shows how MPL interferes with the cell cycle distribution of A2780 cells. OVCAR-3 (FIG. 3a) or A2780 (FIG. 3b) cells were treated with MPL (0, 5, 10 and 25 µmol/L) for 48 hours. Propodium iodide stained cells were analysed for DNA content using flow cytometric analysis. The results (see table) are shown as a percentage of cells in G1, S and G2/M phases. Each value represents mean±SEM of 2 independent experiments.
Figure 4:
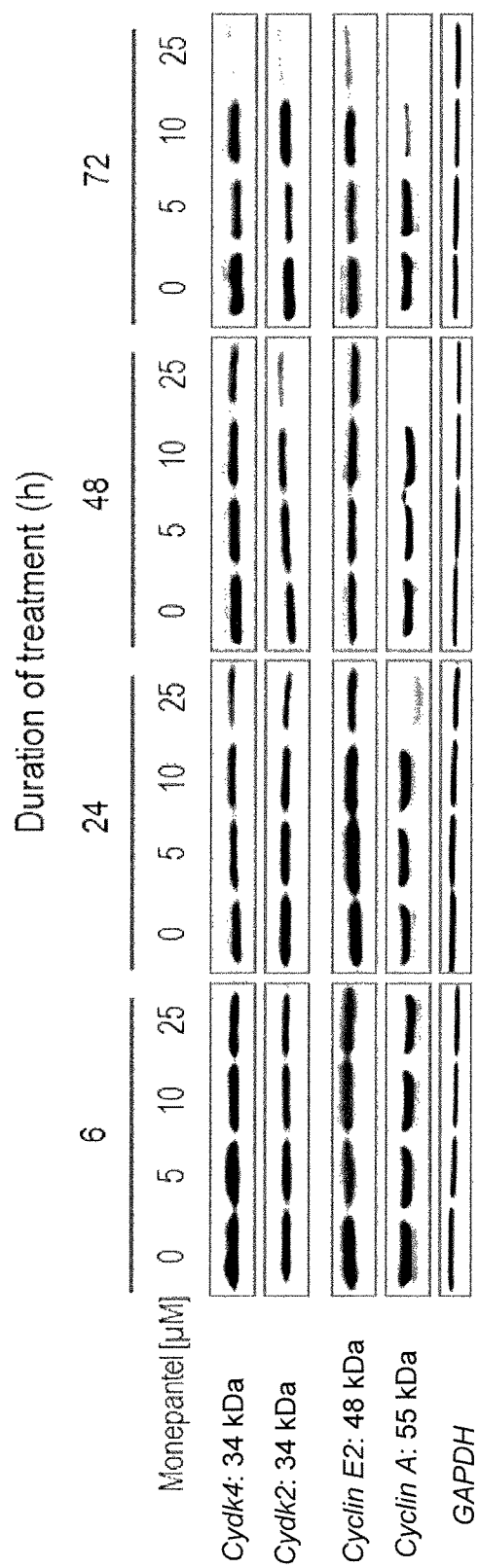
FIG. 4 shows MPL interferes with the expression of cell cycle regulatory proteins cdk2, cdk4 and cyclins E and A. Cells were treated with MPL (0, 5, 10 and 25 µmol/L) for 48 hours. Whole-protein extracts were obtained and separated by electrophoresis and immunoblots were probed with the indicated antibodies. Western blot analysis showing the levels of these proteins in each extract was analysed using the relevant antibodies. The image represents the exposed radiographic film scanned. The house-keeping gene (GAPDH) was used to confirm similar protein loading and blot transfer.

MPL Arrests Cell Cycle Through Down Regulating the Expression of Cyclines and Cycline-Dependent Kinases To investigate the mechanism(s) through which MPL inhibits cell proliferation and colony formation, the effect of the MPL on the cell cycle by means of flow cytometry was examined. It was found that MPL interferes with the cell cycle progression (FIG. 3). Progression of cells exposed to MPL was arrested in the G1 phase in a concentration and time-dependent manner. Accumulation of cells in the G1 phase was accompanied by sharp decline of percentage of cells in the S and G2-M phases. To study the molecular mechanisms involved in the MPL-induced cell cycle arrest, the expression of cell cycle regulatory proteins cdk2, cdk4, cyclins A, and E was examined. MPL treated cells expressed lower levels of cdk2, cdk4, cyclins A, and E (FIG. 4).

MPL Arrests Cell Cycle Through Down Regulating the Expression of Cyclines and Cycline-Dependent Kinases Leading to Induction of PARP-1 Cleavage.

Figure 16:
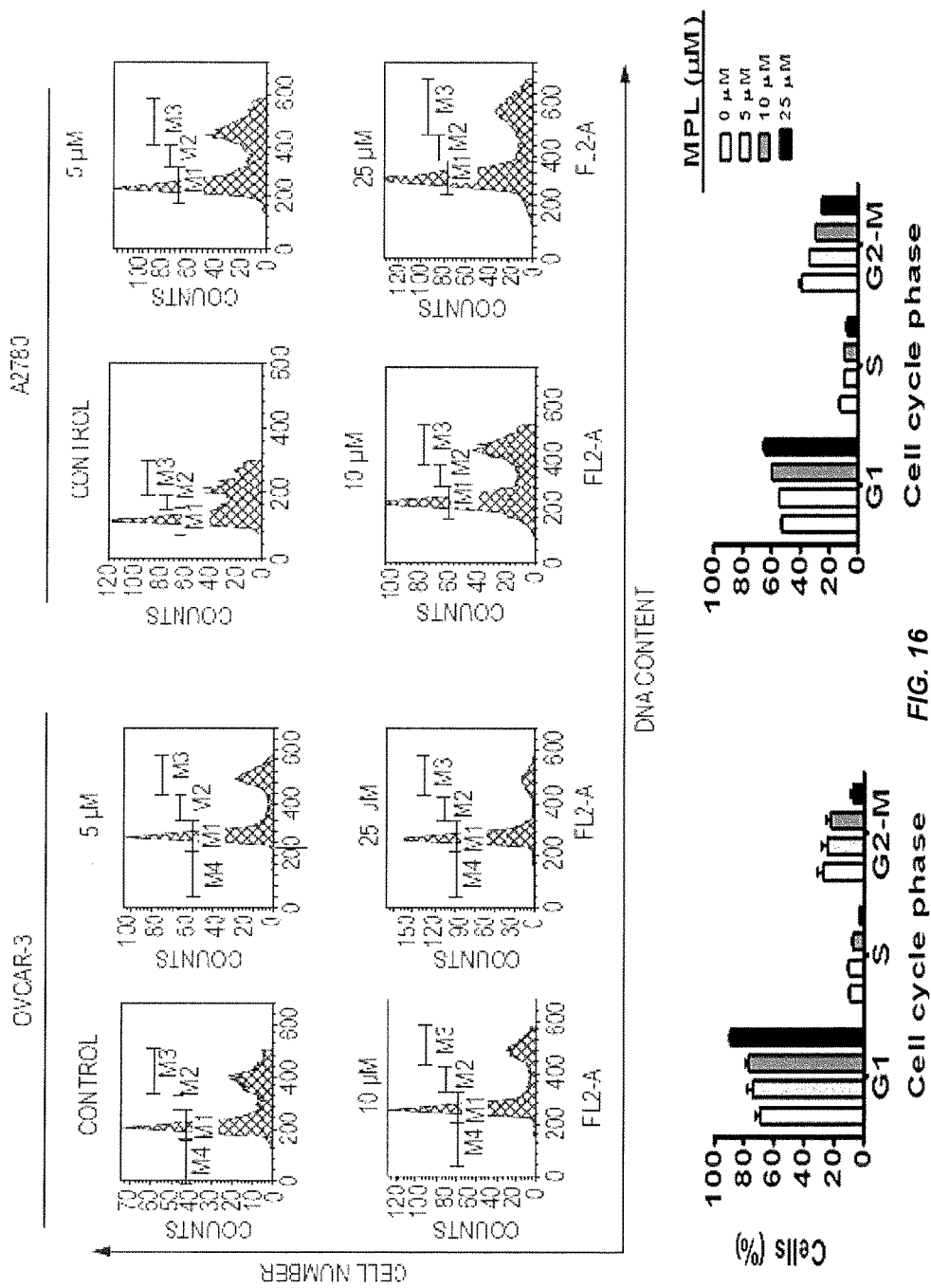
FIG. 16 shows how MPL interferes with the cell cycle progression of ovarian cancer cell lines. OVCAR-3 or A2780 cells were treated with MPL (0, 5, 10, 25 µM) for 48 h and examined by flow cytometric analysis (FACS) after staining the cells with PI. The Fig. and data present MPL-induced change in cell distribution in various phases of the cell cycle, here shown as percentage of cells in G1, S and G2/M phases. Each value represents mean±SEM of 2 independent determinations.
Figure 17:
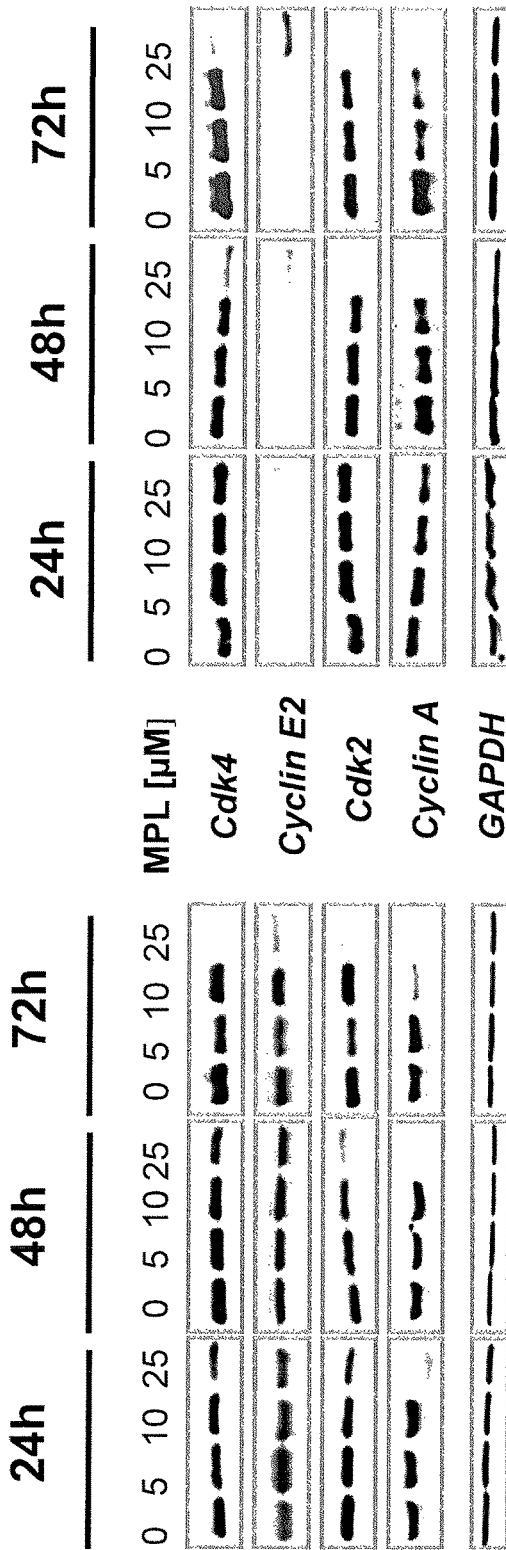
FIG. 17 shows how MPL interferes with the expression of cell cycle regulatory proteins cdk2, cdk4, cyclines E and A. Cells were treated with MPL (0, 5, 10, 25 µM) for 24, 48 h or 72 h. Whole-protein extracts were obtained and separated by electrophoresis, and immunoblots were probed with the indicated antibodies. Western blot analysis showing the levels of these proteins in each extract was analysed using the relevant antibodies. The image represents the exposed radiographic film scanned. The house-keeping gene (GAPDH) was used to confirm similar protein loading and blot transfer.
Figure 22:
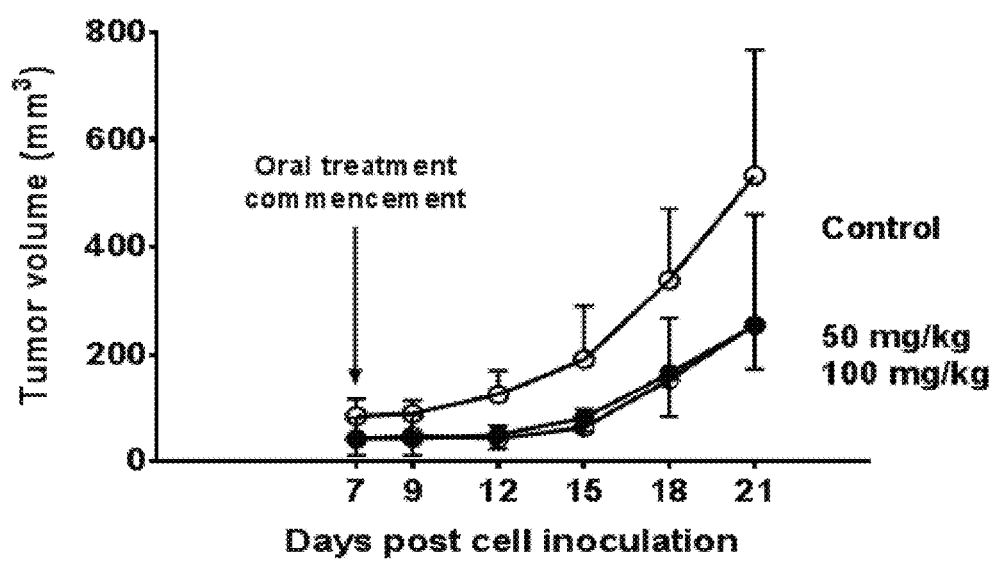
FIG. 22 shows the effect of oral monepantel on tumor growth in nude mice. OVCAR-3 cells were injected s.c. into the left flank of each mouse. Tumor growth was monitored by caliper measurements and tumor volumes were determined of orthogonal diameters, and the estimated tumor volume was calculated based on the formula ½ (Length×Width2), where width is the shorter of the two orthogonal measurements. Treatment was initiated 7 days post tumor cell injection before which, mice were randomized and assigned to treatment or the control group (6 per group). Monepantel suspended in 0.5% HPMC was administered orally (100 µL) at 50 or 100 mg/kg thrice weekly. Control group were treated orally with the vehicle only.

To find out the mechanism(s) through which MPL inhibits cell proliferation and colony formation, the effect of MPL on the cell cycle was examined by means of flow cytometry (FACS). It was found that MPL interferes with the cell cycle progression (FIG. 22). In cells exposed to MPL cell cycle was arrested in the G1 phase in a concentration and time-dependent manner. Accumulation of cells in the G1 phase was accompanied by sharp decline in percentage of cells in the S and G2-M phases. To study the molecular mechanisms involved in the MPL-induced cell cycle arrest, the expression of cell cycle regulatory proteins cdk2, cdk4, cyclins A, and E was examined. MPL treated cells expressed lower levels of cdk2, cdk4, cyclin E, and cyclin A (FIGS. 4 and 16).

MPL Induces PARP-1 Cleavage

Figure 5:
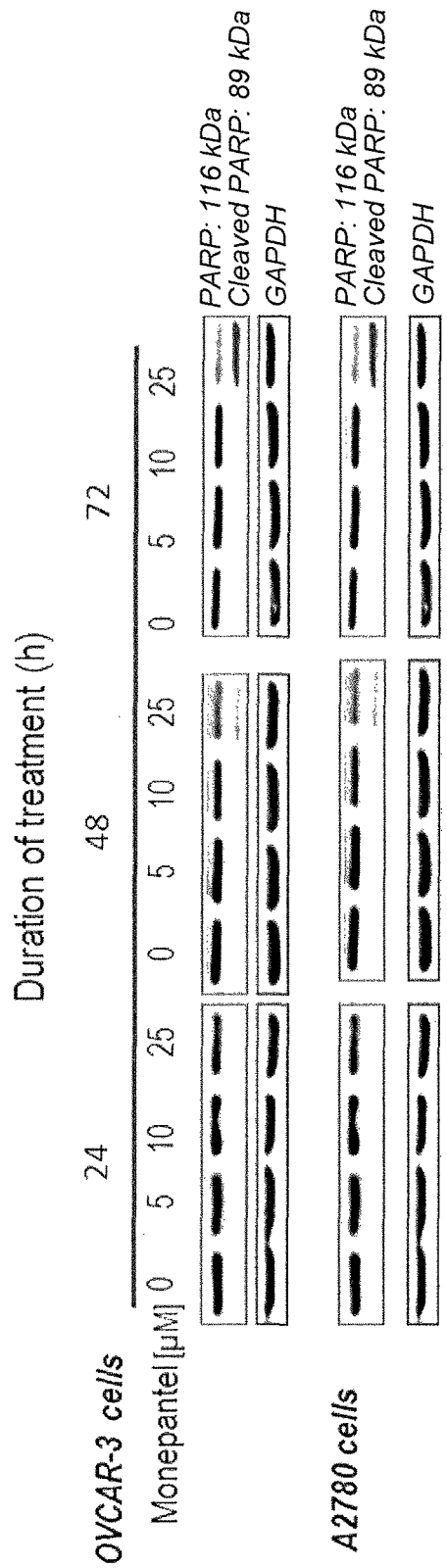
FIG. 5 shows an immunoblot analysis of PARP and cleaved PARP in MPL treated cells. OVCAR-3 and A2780 cells grown under cell culture conditions were incubated with various concentrations of MPL [0, 5, 10, 25 µM] for 24, 48 or 72 hours. Cell lysates were then prepared and analysed by western blotting for the determination of PARP and cleaved PARP.

To investigate whether the MPL-induced cell death involves cleavage of PARP, western blot analysis of lysates of MPL-treated cells for PARP-1 and cleaved PARP-1 was carried out. Cleavage of PARP-1 promotes apoptosis by preventing DNA-repair-induced survival. PARP helps cells to maintain their viability and hence cleavage of PARP facilitates cellular disassembly and serves as marker of cells undergoing apoptosis. FIG. 5 shows that PARP was cleaved in MPL treated cells.

MPL Induces PARP Cleavage

Figure 18:
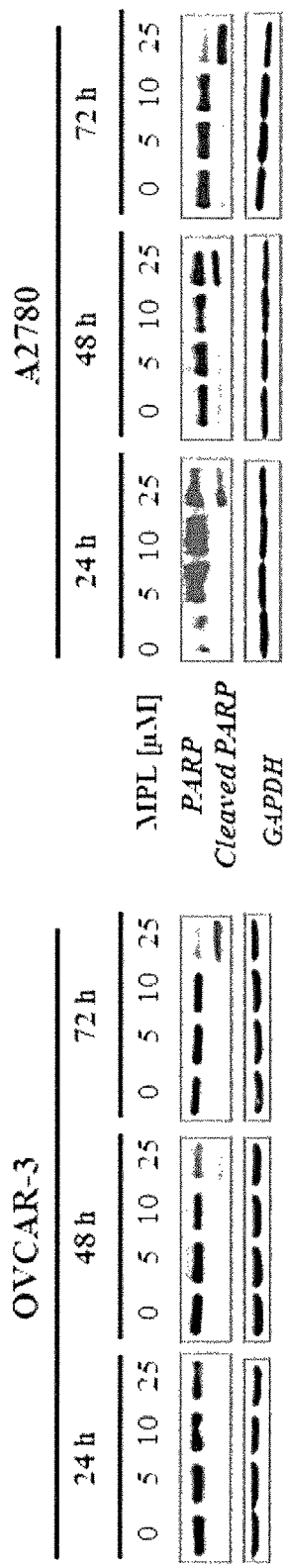
FIG. 18 shows how MPL cleaves PARP. Exposure of OVCAR-3 or A2780 cells to MPL (0, 5, 10, 25 µM) for 24, 48 or 72 h causes cleavage of PARP, which leads to cellular disassembly and serves as a marker of dying cells.

Western blot analysis of cell lysates prepared from MPL treated OVCAR-3 and A2780 cells showing highly induced cleavage of PARP representing cell death (FIG. 18).

MPL Reduces Cellular ATP Levels

Figure 19A:
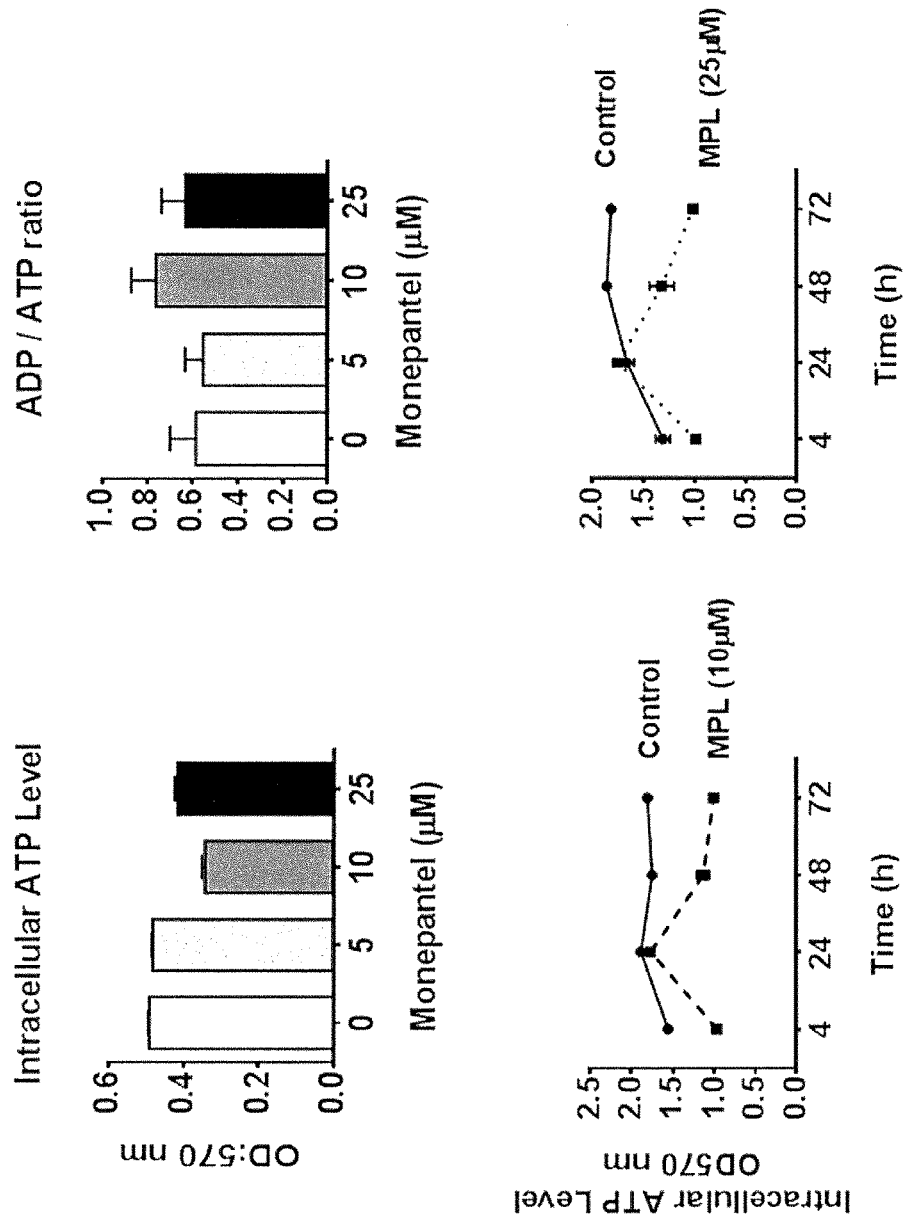
FIG. 19A and FIG. 19B show how MPL decreases ATP levels. Exposure of OVCAR-3 or A2780 cells to MPL (0, 5, 10, 25 µM) for 24, 48 or 72 h causes cleavage of PARP, which leads to cellular disassembly and serves as a marker of dying cells.
Figure 19B:
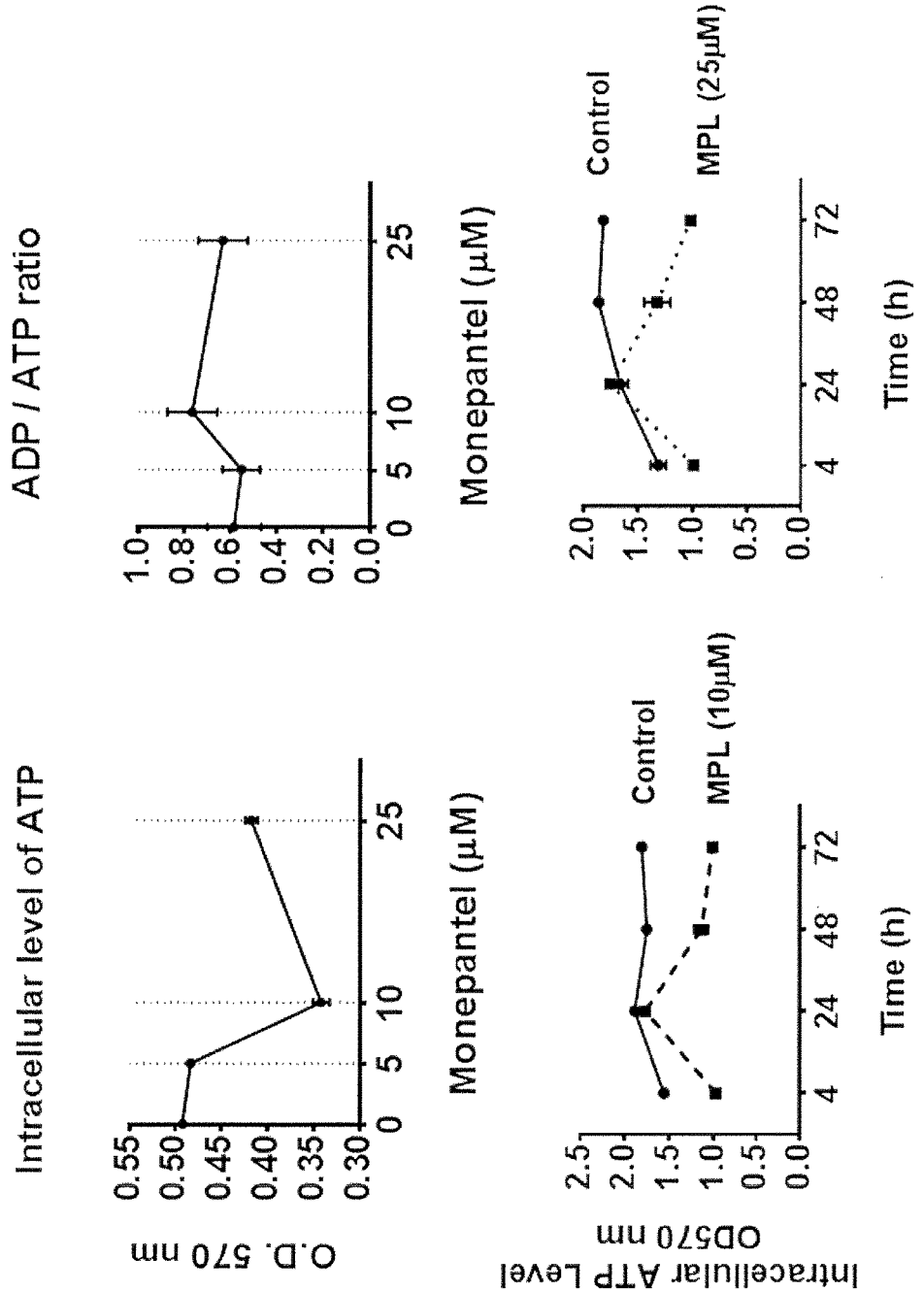

As depicted in FIGS. 19A and 19B, treatment of OVCAR-3 or A2780 cells with MPL causes a reduction in ATP levels found in the cell.

MPL Induces Autophagy

Figure 6:
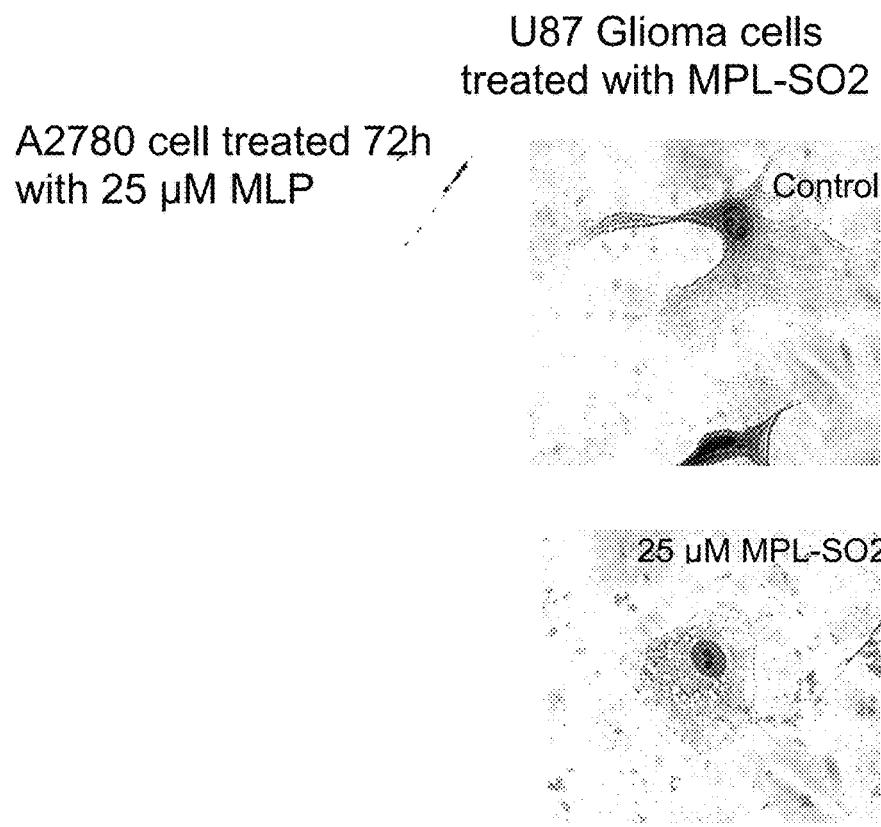
FIG. 6 shows that treatment of A2780 ovarian cancer cells with MPL or U87 glioma cells with MPL-SO$_2$ lead to the formation of vacuoles suggesting that MPL and MPL-SO$_2$ induce autophagy in these cells. Autophagy is a characteristic of mTOR inhibition.
Figure 7:
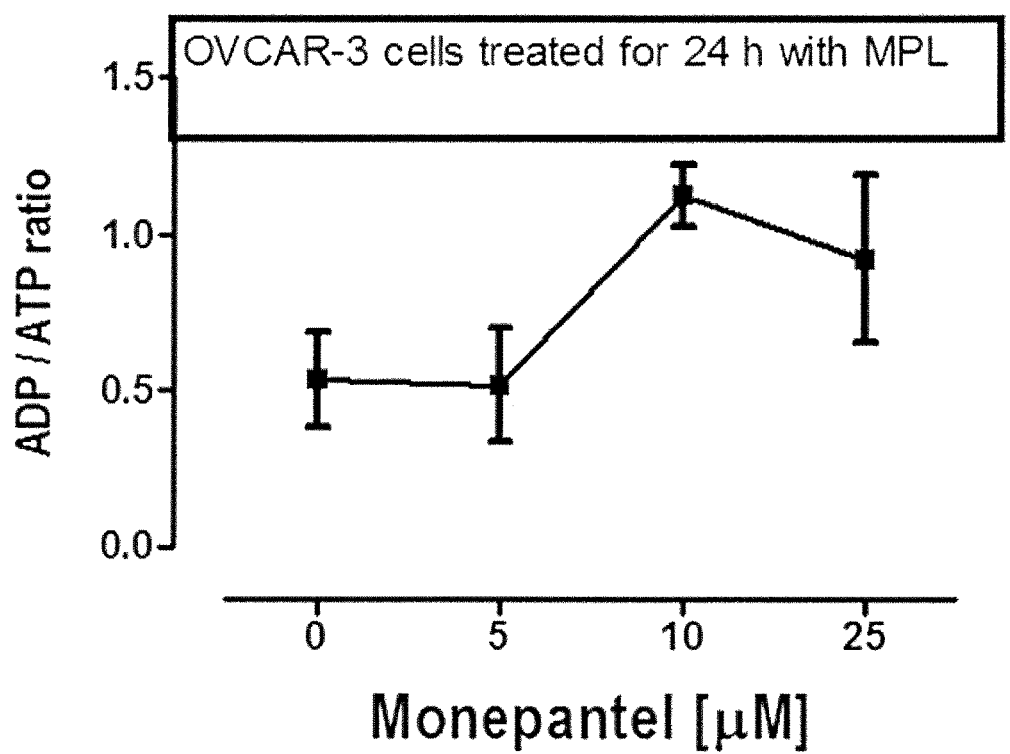
FIG. 7, consistent with that shown in FIG. 6, shows that MPL treatment reduces the cellular ratio of ADP/ATP, which is another indicator of cellular autophagy.

FIG. 6 shows that the treatment of cells with MPL leads to the formation of vacuoles suggesting that MPL may be inducing autophagy in these cells. FIG. 7 shows that MPL treatment reduces the cellular ratio of ADP/ATP, which is another indicator of cellular autophagy.

MPL Suppresses Rate of s.c. Xenografts Growth in Nude Mice

Figure 20:
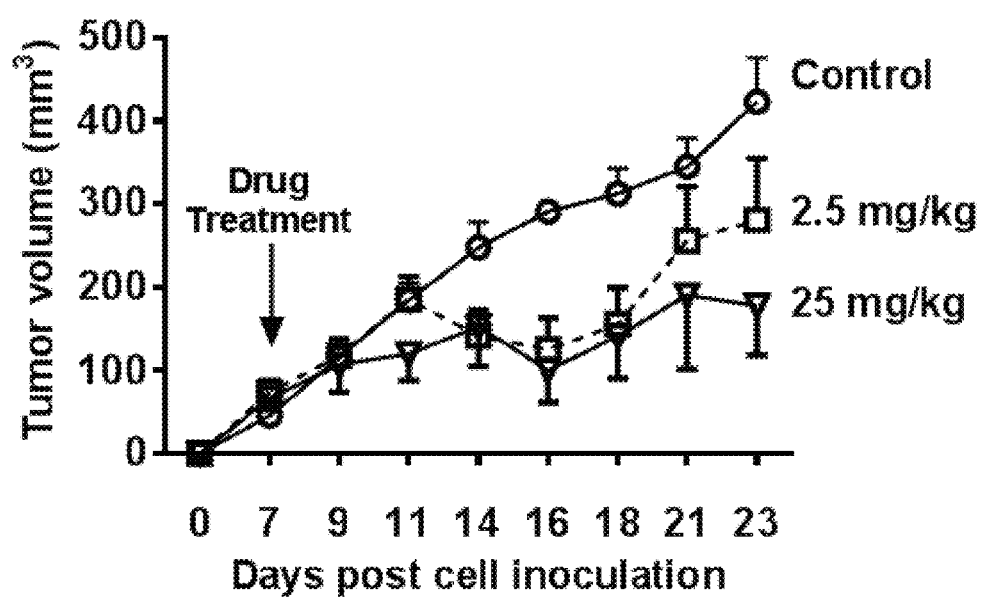
FIG. 20 shows the effect of i.p. (intraperitoneal) administered monepantel on s.c. (subcutaneous) tumor growth in nude mice. 2.5 million log-phase growing OVCAR-3 cells were injected s.c. into the left flank of each mouse. Tumor growth was monitored by caliper measurements and tumor volumes were determined through measuring orthogonal diameters. Estimated tumor volume was calculated based on the formula ½ (Length×Width2), where width is the shorter of the two orthogonal measurements. Treatment was initiated 7 days post tumor cell injection before which, mice were randomized and assigned to treatment or the control group (6 per group). Monepantel suspended in 0.5% HPMC was administered i.p. at 2.5 or 25 mg/kg thrice weekly. Control group were treated with the vehicle only.
Figure 21:
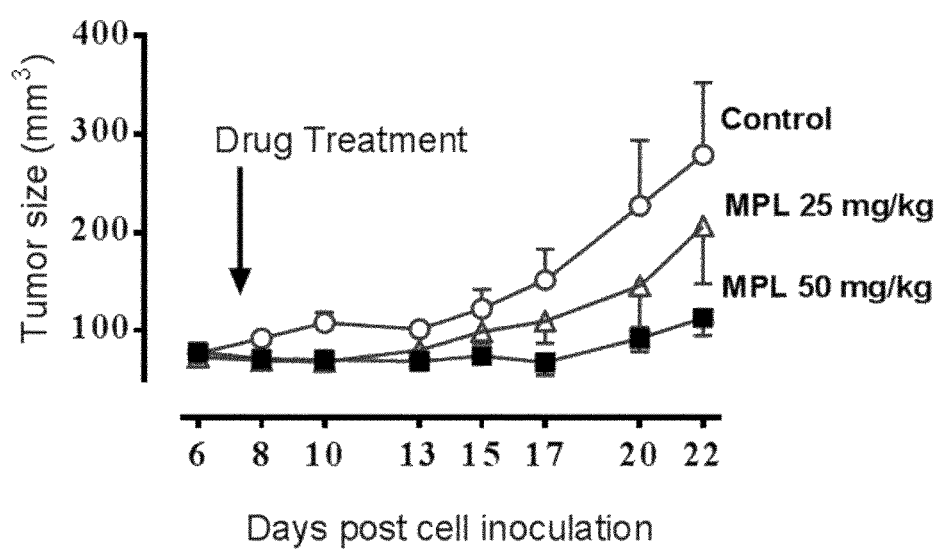
FIG. 21 shows the effect of i.p. administered monepantel on s.c. tumor growth in nude mice. Log-phase growing OVCAR-3 cells were injected s.c. into the left flank of each mouse. Tumor growth was monitored by caliper measurements and tumor volumes were determined through measuring orthogonal diameters. Estimated tumor volume was calculated based on the formula ½ (Length×Width2), where width is the shorter of the two orthogonal measurements. Treatment was initiated 7 days post tumor cell injection before which, mice were randomized and assigned to treatment or the control group (6 per group). Monepantel suspended in 0.5% HPMC was administered i.p. at 25 or 50 mg/kg thrice weekly. Control group were treated with the vehicle only.
Figure 23:
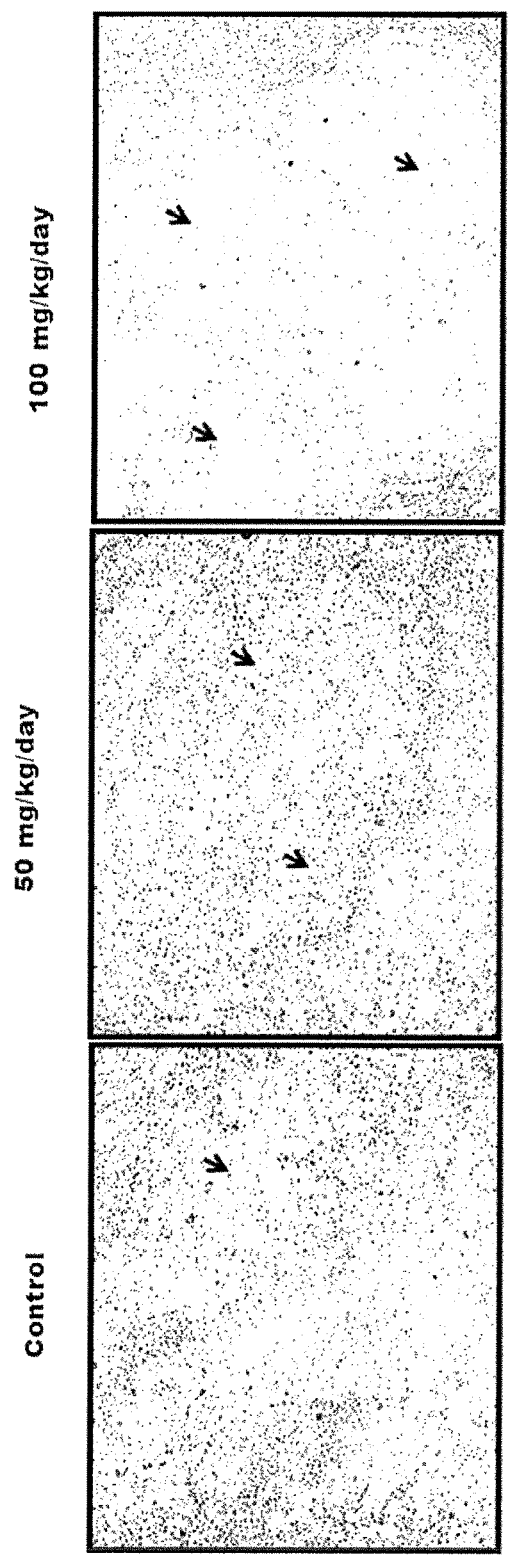
FIG. 23 shows how MPL induces necrosis in tumor tissues. Tumor tissue from subcutaneous xenografts in nude mice were treated with MPL administered orally on alternate days at 50 or 100 mg/kg/day. Histological images of tumors are shown in hematoxylin and eosin staining (H&E; top row), indicating profound drug-induced necrosis (black arrow head; magnification ×10). A representative image of tumor histology from tumors excised from MPL treated mice demonstrating extensive necrosis at the higher dose of 100 mg/kg (s.c. tumor, oral treatment, ×3 weekly for 2 weeks).
Figure 24:
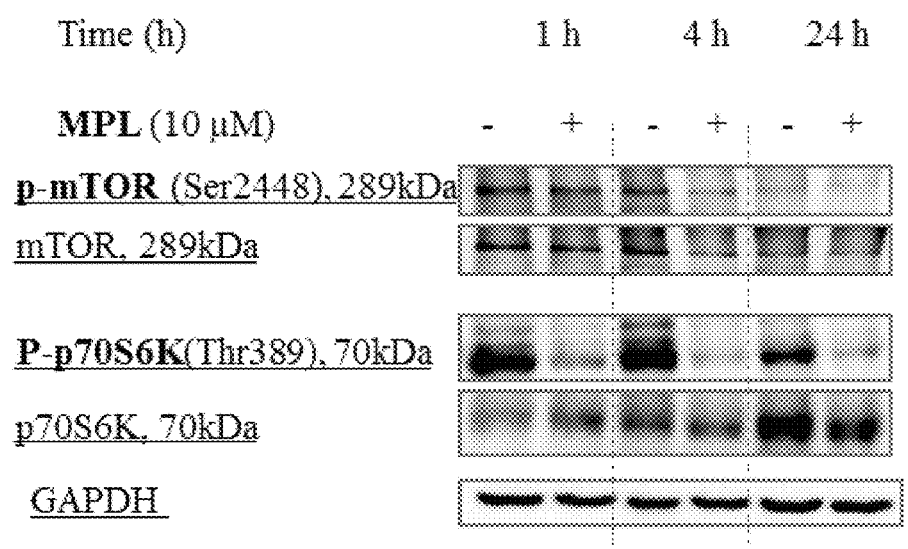
FIG. 24 shows OVCAR-3 cells treated with 10 µM MPL for indicated time points under cell culture conditions. Western blot analysis of cell lysates prepared from OVCAR-3 cells treated with 10 µM MPL for 1, 4 or 24 hours under cell culture conditions. Results demonstrate inhibition of phosphorylation [activation] of both mTOR and its downstream signaling pathway p70S6K.
Figure 25:
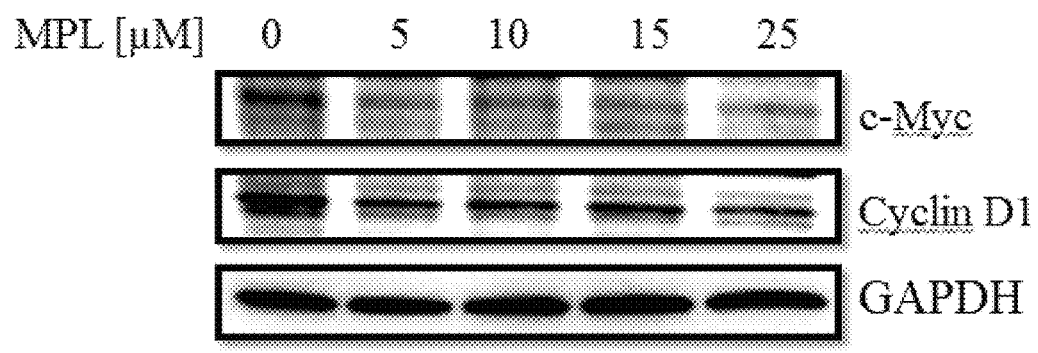
FIG. 25 shows protein expression in human ovarian OVCAR-3 cells treated in vitro with MPL Western blot analysis of cell lysates prepared from OVCAR-3 cells treated with 0, 5, 10, 15 and 25 µM MPL for 48 hours under cell culture conditions. Results demonstrate down-regulation of c-Myc and cyclin D1 expression.
Figure 26:
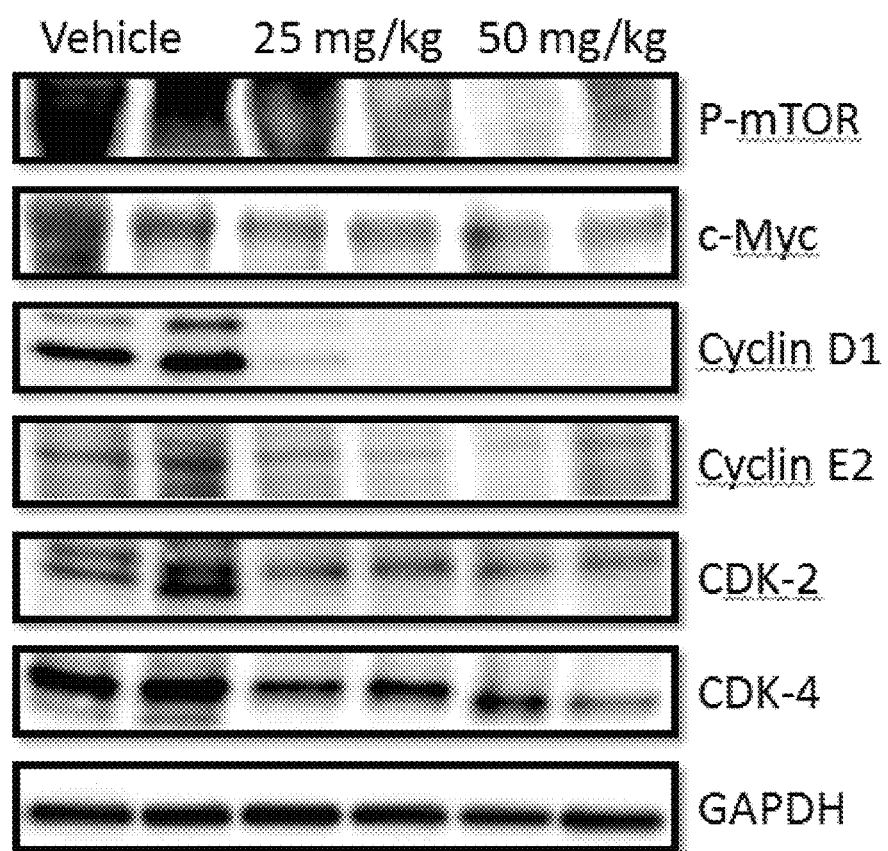
FIG. 26 shows the inhibitory effect of MPL on tumor expression of mTOR related signaling in MPL treated OVCAR-3 tumors. Western blot analysis of tumor lysates prepared from s.c. grown OVCAR-3 tumors in female nude mice. Mice were treated from day 8 post cell inoculation i.p. for 3 weeks with MPL (25, 50 mg/kg suspended in 0.5% HPMC given i.p.) or the vehicle (0.5% HPMC). 24 hours after the last dose, tumors were excised and frozen at −80° C. Western blot analysis of tumors demonstrate suppression of mTOR signaling. Protein expression of mTOR together with c-Myc, cyclins D1 and E2 and CDKs 2 and 4 were suppressed in tumors excised from MPL treated mice.
Figure 27A:
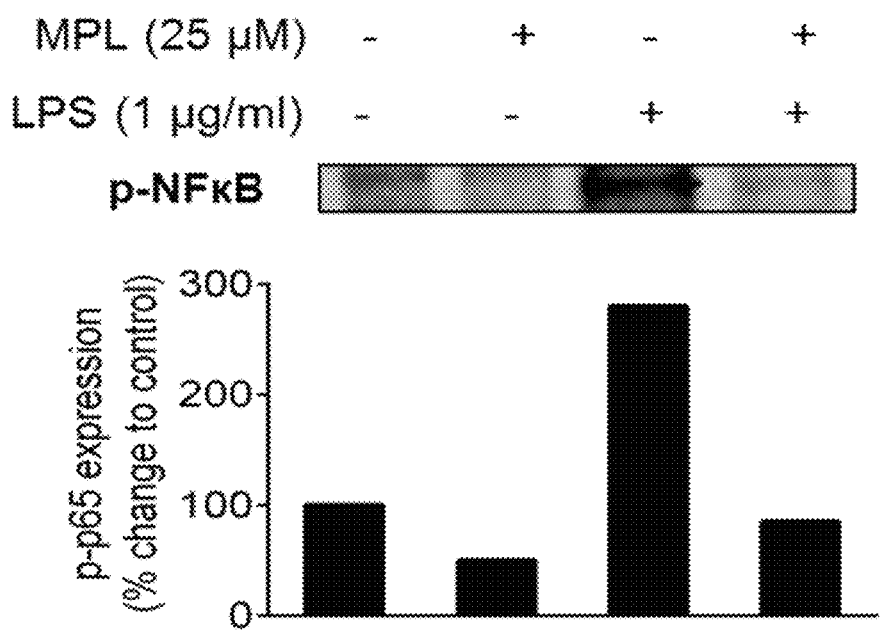
FIGS. 27A and 27B show the inhibitory effect of MPL on NF-κB p65 phosphorylation.
Figure 27B:
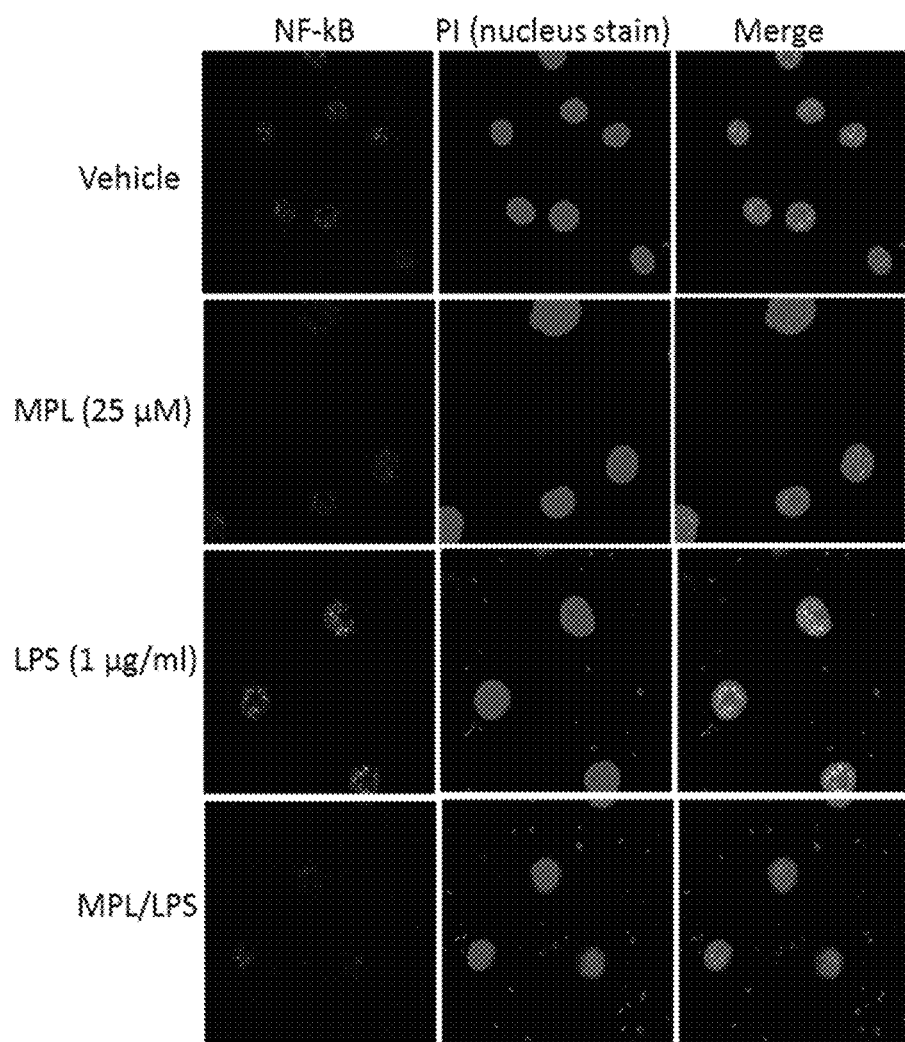
Figure 28:
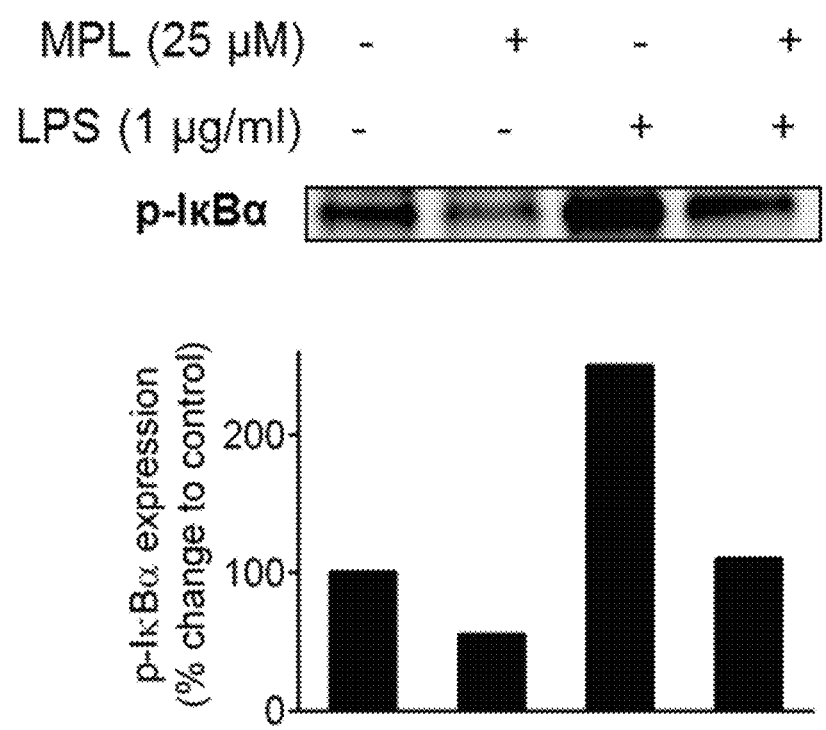
FIG. 28 shows the inhibitory effect of MPL on IκB-α phosphorylation.
Figure 29:
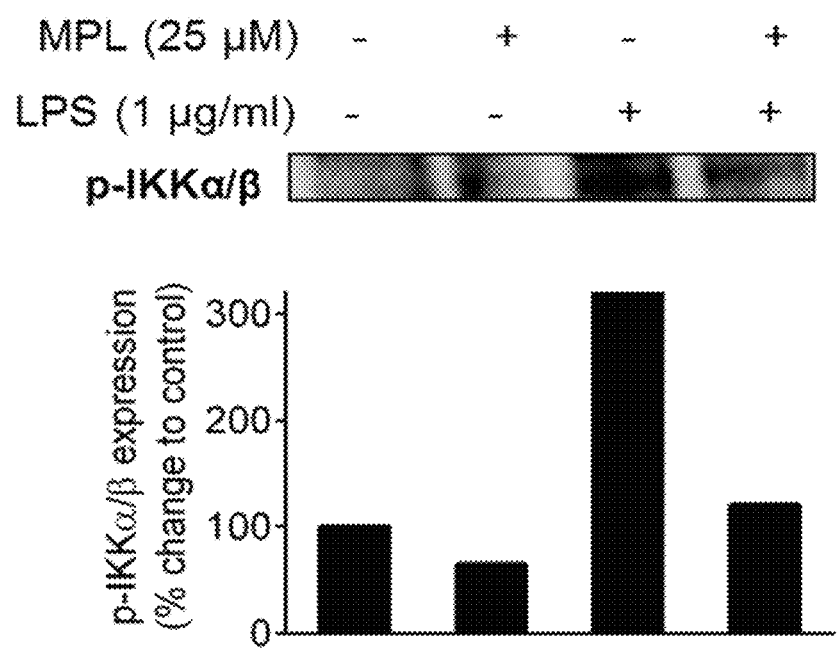
FIG. 29 shows the inhibitory effect of MPL on IKK phosphorylation.
Figure 30:
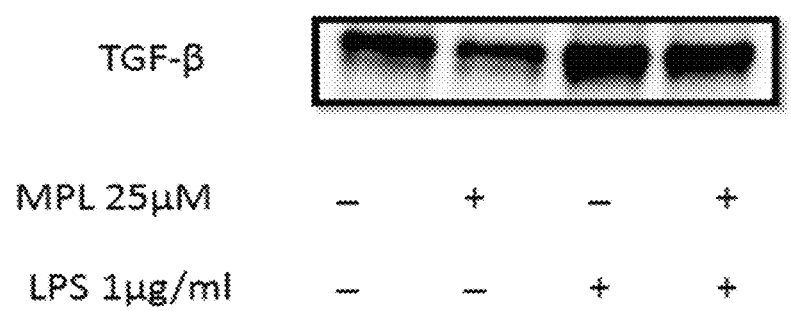
FIG. 30 shows that MPL causes down regulation of IL-6 expression.
Figure 31:
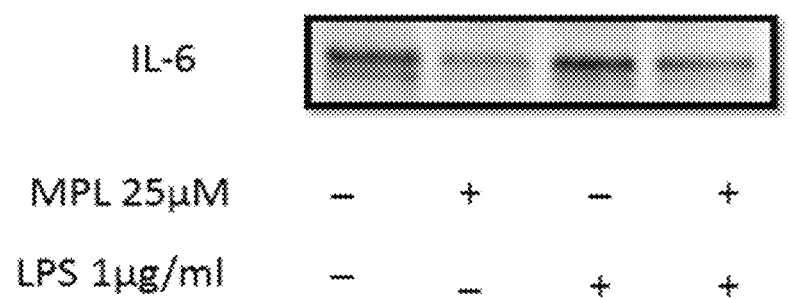
FIG. 31 shows that MPL causes down regulation of TGF-β expression.
Figure 32:
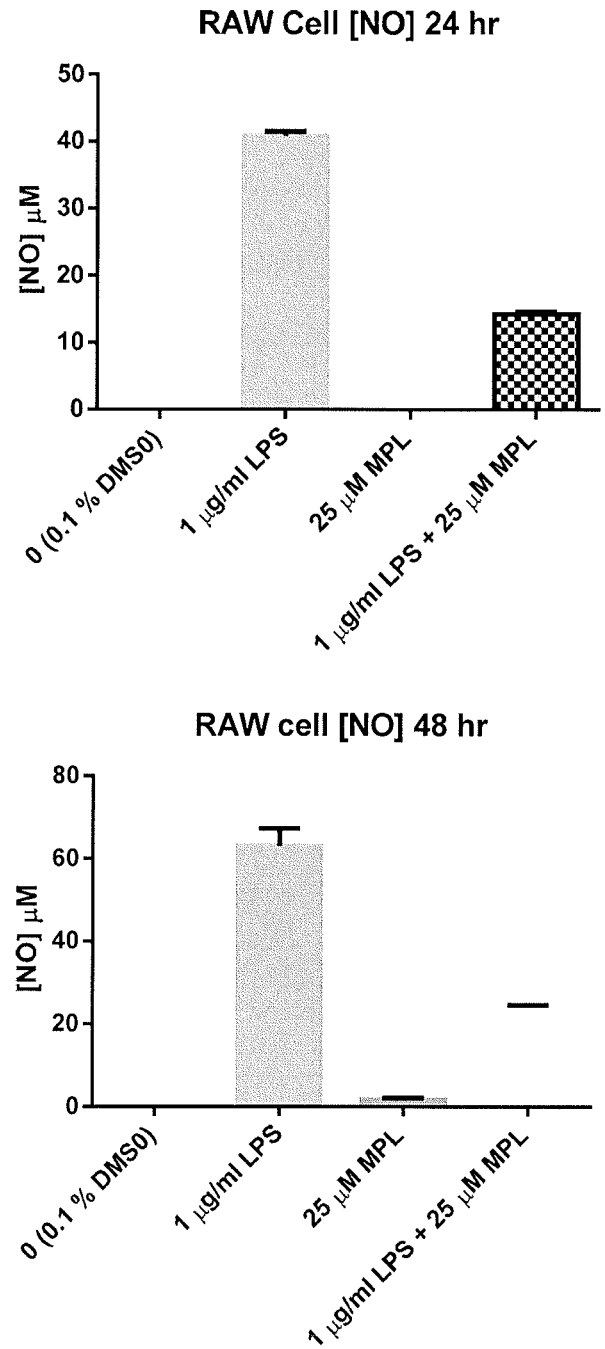
FIG. 32 shows that MPL abrogates NO expression.

FIGS. 20-22 show in vivo testing of the MPL in nude mice. Mice bearing OVCAR-3 tumors were treated either first i.p. or, as according to the last experiment, orally. Results obtained reveal the activity of the administered doses and in particular the 50 mg/kg dose (both i.p. and oral) in profoundly retarding tumor growth in these animals. Tumor histology revealed massive areas of tumor cell death (FIG. 23).

The inhibition of cell proliferation coupled with suppression of colony formation, and the in vivo results show a growth regulatory effect for MPL. MPL interference is shown with the cell cycle progression through reducing expression of cell cycle regulatory proteins A and E2 together with their kinases cdk2 and cdk4. In the normal cell, the transition from one phase to another occurs in an orderly fashion well regulated by various proteins. Cyclin-dependent kinases (CDK) are the key regulatory proteins that are activated at specific points of the cell cycle thus playing a crucial role in cell cycle progression. These require different cyclins at different phases of the cycle. Cyclins A, D and E are required for the G1 and G1 transition to S phase of the cell cycle. Of the various CDKs identified so far, CDK2 and CDK4 seem essential for entry in G1 and G1-S transition. Cyclins A and E bind to CDK2 while cyclin D binds to CDK4 and CDK6. Cancer is one of several diseases considered to be a cell cycle related phenomenon.

Results presented in FIGS. 20-22 demonstrate MPL activity in suppressing s.c. tumor growth in female nude mice. The initial trial revealed dose-dependent activity of i.p. MPL administration. The 25 mg/kg dose was particularly effective. On this basis, the next trial was conducted using 25 and 50 mg/kg doses under the same conditions as before. The 50 mg/kg dose was more effective in retarding tumor growth in these animals. As an anti-parasitic agent, MPL has been shown to be orally effective in a number of animal models. The oral therapeutic activity of 50 and 100 mg/kg doses of MPL were tested. In all three pilot trials, MPL was prepared in 0.5% HPMC and administered as a suspension. Examination of tumor tissue from these in vivo trial revealed areas with extensive necrosis in the MPL treated tumors (FIG. 23).

The effects observed are not limited to ovarian cancer, as shown in Tables 1 and 2, and MPL effectively suppresses in vitro cell proliferation in a variety of cell lines representing various cancers including, glioma, prostate, breast, mesothelioma, liposarcoma, fibrosarcoma (see Tables 1 and 2).

Another important observation is the activity of MPL against chemo-resistant cell lines. Ovarian chemo-resistant cells, glioma temozolimide resistant cells and breast cancer tamoxifen resistant cells were all sensitive to MPL antiproliferative action.

In conclusion, the results demonstrate that in cancer cell-lines, MPL and potentially its metabolites and analogues (AADs):

1—Inhibit cell proliferation;
2—MPL-induced inhibition is neither positively nor negatively affected by pre-treatment with nicotinic agonists or antagonists indicating that the mode of action is not nicotine receptor mediated;
2—inhibit colony formation;
3—Arrest cell cycle [G1 phase];
4—Down regulate cell-cycle regulatory proteins (CdK2, CdK4, cyclin A, cyclin E);
5—Blocks thymidine incorporation into the cell thus inhibits DNA synthesis;
6—Reduces cellular ATP levels;
7—Causes progressive autophagy as confirmed by conversion of LC3B-I into LC3B-II;
8—Autophagy was microscopically clear in both ovarian and glioma cancer cell lines;
9—MPL also induces cleavage of PARP-1 and thus cell death;
10—This is confirmed by in vivo data showing dose-dependent suppression of tumors in nude mice bearing s.c. tumors;
11—Both i.p. and oral routes of administration were effective.

Furthermore, MPL inhibits proliferation of cells resistant to some standard chemotherapy.

mTOR and Autophagy

Another aspect of the present application is the role of autophagy in cancer and in neurodegenerative disease. In neuronal cells with abnormal rapid apoptosis causing neurodegenration, autophagy serves as a mechanism to protect neurones from accelerated cell death.

Autophagy, or cellular self-digestion, is a cellular pathway involved in protein and organelle degradation, with an astonishing number of connections to human disease and physiology. For example, autophagic dysfunction is associated with cancer, neurodegeneration, microbial infection and ageing. Paradoxically, although autophagy is primarily a protective process for the cell, it can also play a role in cell death in cancer cells.

mTOR is a major negative regulatory axis of autophagy. Direct inhibitors of mTOR and those of pathways activating mTOR, subsequently induce autophagy. The mTOR kinase responds to growth factors and nutrient levels to regulate cellular growth and autophagy. Inhibition of mTOR causes autophagy. Autophagy protects cells from damage leading to neurodegeneration.

Autophagy, the major degradative pathway for organelles and long-lived proteins, is essential for the survival of neurons. Mounting evidence has implicated defective autophagy in the pathogenesis of several major neurodegenerative diseases, particularly Alzheimer's disease (AD). The findings from the studies reviewed suggest that autophagy is altered in the early stage of the disease, and dysfunction in autophagy may play an important role in the pathological process of AD.

Autophagy Protects Cells from Damage Leading to Neurodegeneration mTOR/Autophagy in Neurodegenerative Diseases Alzheimer's Disease The buildup of Abeta and tau is believed to directly cause or contribute to the progressive cognitive deficits characteristic of Alzheimer disease. It has been shown that mTOR may play a role in Abeta and tau induced neurodegeneration.

The mTOR pathway plays a central role in controlling protein homeostasis and hence, neuronal functions. Indeed, mTOR signaling regulates different forms of learning and memory. Rapamycin rescues cognitive deficits and ameliorates Abeta and Tau pathology by increasing autophagy. Similarly, several mTOR signaling components may be potential biomarkers of cognitive impairment in the clinical diagnosis of AD. Thus, through the control of autophagy-lysosome protein degradation, mTOR-related agents (such as MPL) are anticipated to be important therapeutic agents for AD.

Huntington Disease

Huntington disease is one of nine inherited neurodegenerative disorders caused by a polyglutamine tract expansion. Expanded polyglutamine proteins accumulate abnormally in intracellular aggregates. It is shown that mTOR is sequestered in polyglutamine aggregates in cell models, transgenic mice and human brains. Sequestration of mTOR impairs its kinase activity and induces autophagy, a key clearance pathway for mutant huntingtin fragments. This protects against polyglutamine toxicity, as the specific mTOR inhibitor rapamycin attenuates huntingtin accumulation and cell death in cell models of Huntington disease, and inhibition of autophagy has the converse effects.

mTOR is also involved in inlnflammation, immunosuppression and neurodegenerative diseases.

The Activity of MPL on Inflammatory Pathway NF-κB and its Downstream Targets

The transcription factor NF-κB has been of interest for inflammatory-mediated responses, primarily because several mediators and cytokines cause the activation of this transcription factor. Furthermore, activation of the NF-κB transcription family plays a central role in inflammation through its ability to induce transcription of proinflammatory genes. The link between the activation of NF-κB and inflammation has been shown in various human diseases and in animal models of disease. In addition, the role of NF-κB in mediating inflammation has been established using genetic approaches or with chemical inhibitors.

NF-κB is present in the cytosol as an inactive form bound to the inhibitory protein IκBα. When stimulated by appropriate extracellular signals IκBα is phosphorylated by IKK, which results in proteasome-mediated degradation of IκBα. Then the active complex of NF-κB is librated and translocates to nucleus to mediate transcription of its target genes. The IKK complex is activated either through autophosphorylation or via phosphorylation by a series of mitogen-activated kinases (MAP3K) in response to divergent stimuli such as lipopolysaccharides (LPS), IL-1β, Tumor necrosis factor (TNF)-α and TGF-β.

FIGS. 27 to 32 shows the influence of MPL on NF-κB signal transduction pathway. LPS-stimulated RAW 264.7 cells macrophages were used as an in vitro model system for inflammation.

It was observed that MPL decreased NF-κB activation in these cells as assessed by immunocytochemistry and Western blot analysis. This effect could be confirmed by inhibition of phosphorylation and nuclear translocation of NF-κB p65 and also inhibition of phosphorylation of IKK and IκB-α. The inhibitory effect of MPL was also observed on the expression of IL-6, TGF-β and also nitric oxide (NO), which are all inflammatory mediators regulated by NF-κB.

The results show that MPL inhibits cellular mechanisms, which are important in reducing inflammation and that MPL is affecting important pathological pathways which are not related to cancer.

The results clearly show that MPL inhibits cellular mechanisms, which are important in a response to inflammation and that MPL is affecting on important pathological pathways which are not related to cancer.

Discussion mTOR, the mammalian Target Of Rapamycin, was named based on the precedent that TOR was first discovered via genetic and molecular studies of rapamycin-resistant mutants of *saccharomyces cerevisiae* that identified FKBP12, Tor1, and Tor2 as the targets of rapamycin and provided robust support that the FKBP12-rapamycin complex binds to and inhibits the cellular functions of Tor1 and Tor2.

Rapamycin arrested fungal activity at the G1 phase of the cell cycle. In rats, it suppresses the immune system by blocking the G1 to S phase transition in T lymphocytes. In humans, it is used as an immunosuppressant following organ transplantation. mTOR integrates the input from upstream pathways, including insulin, growth factors (such as IGF-I and IGF-2), and amino acids. mTOR also senses cellular nutrient, oxygen, and energy levels. The mTOR pathway is dysregulated in human diseases, such as diabetes, obesity, depression, and certain cancers. Rapamycin is a bacterial product that can inhibit mTOR by associating with its intracellular receptor FKBP12. The FKBP12-rapamycin complex binds directly to the FKBP12-Rapamycin Binding (FRB) domain of mTOR, inhibiting its activity.

Although the mTOR pathway has been identified as an important element in many diseases including cancer, to date only rapamycin is in extensive clinical use and despite its launch in the 90s, new mTOR products have limited clinical use. Similarly, despite rapamycin's ability to interfere with the mTOR pathway, it is still only useful for treatment of organ rejection. The present invention identifies a new class of mTOR inhibitors that target different components of the mTOR pathway to rapamycin, thereby opening up broader treatment options for a number of major diseases.

As shown in Table 1, MPL was also tested on HUVECs. It was found that the IC50 value is about 10 times higher than the IC50 value in OVCAR-3, which reflects the higher cytotoxic potency of MPL on cancerous than non-cancerous cells.

In colony formation assays, MPL suppressed formation of colonies by ovarian cancer cell lines growing on agar plates in a concentration-dependent manner and therefore further demonstrates the efficacy of MPL to inhibit the growth of cancer cells.

In addition, it has been shown that irrespective of the p53 status of the [OVCAR-3 (mutated), SKOV-3 (null) and A2780 (wild type)] cells, MPL exerted its anti-cancer effects (albeit at different potencies). This suggests that MPL would be effective in epithelial ovarian cancers irrespective of their tumor p53 status. This finding may be of importance as p53 mutation is highly common in a wide range of cancers.

It is to be understood that the effects shown by MPL may be extended to other types of cancers in addition to ovarian cancer.

The mammalian cell cycle is governed by sequential activation of the Cdks. Progression through the G1 phase and entry into the S phase is regulated by Cdk2 complexed with cyclin A and cyclin E. Therefore, suppressing the expression of these regulatory proteins disrupts the cell cycle progress.

Inhibition of cell proliferation and colony formation is concentration-dependent on MPL. A possible mechanism by which MPL disrupts cell cycle progression is down-regulation of cell cycle regulatory proteins E and A and the cycline-dependent kinases Cdk4 and Cdk2, causing G1 arrest. As a result of G1 arrest, cells do not progress onto the next stage of the cycle as shown by a dramatic reduction of cells in the S and G2-M phases over time. The percentage of cells in the G2-M phase of the vehicle treated group was more than three times higher than those in the group treated with 25 μM MPL.

Furthermore, the evidence of autohphagy in the cancer cell lines treated with MPL strongly suggests that the cells are irreversibly exiting the cell-cycle via a G0 phase cell cycle arrest.

Further Discussion

Cumulative evidence supports the hypothesis that mTOR acts as a 'master switch' of cellular catabolism and anabolism, signalling cells to expand, grow and proliferate. Although it is found in virtually all mammalian cells, it is particularly important in tumour cells that proliferate and invade aggressively.

Treatments targeted against cellular signalling pathways have shown promise in the management of solid tumours and hematological malignancies. mTOR was shown to be a key kinase acting downstream of the activation of the phosphatidylinositol 3 kinase (PI3K).

Agents that specifically inhibit mTOR are currently being developed as potential anti-tumor drugs.

mTOR inhibitory agents essentially interrupt cell cycle progression through induction of G1 phase arrest. Rapamycin is the prototype mTOR inhibitor.

The mTOR biology has provided insights into the role of mTOR in various cancers. An active mTOR coordinates a response in cell growth directly through its effects on cell cycle regulators and indirectly by sustaining nutrient supply into the cell through the production of nutrient transporters and also through the promotion of angiogenesis. A primary way that mTOR exerts its regulatory effects on cell proliferation is by controlling the production of cyclin D1. mTOR provides the adequate nutrient support to sustain abnormal cell growth and proliferation. Given that the mTOR pathway is deregulated in a number of cancers, mTOR inhibitors are expected to exert broad anticancer therapeutic effects.

Surrogate molecular markers can be used to monitor biological effects of mTOR inhibitors such as rapamycin derivatives and narrow down biologically active doses in patients. These may include expression of cyclin D1, cyclin E, phosphorylation of P70S6K or expression of caspase 3 and c-Myc. Cyclin D1 is a proto-oncogene whose gene amplification and protein over-expression are frequently observed in tumor cells. Cyclin D1 induces the progression of the cell cycle from G1 to S.

It has been shown that MPL arrests cell cycle progression at the G1 phase. According to the present invention, data is presented from MPL treated tumor bearing mice showing dramatic down-regulation of cyclin D1. Furthermore, tumor expression of cyclin E another important intermediate of the mTOR signalling pathway and cell cycle progression is also suppressed in MPL treated tumors. Cyclins D and E, known as G1 cyclins, bind to CDK4 and CDK2 respectively and facilitate the transition from G1 to S phase. Loss of cyclin D1 in ovarian cancer cells is sufficient to induce G1 cell cycle arrest and this strategy is not impeded by the presence of cyclin E2. It has even been suggested that, cyclin D1 is a sufficient therapeutic target in ovarian cancer cells. It is well established that c-Myc affects the cell cycle at multiple points including cyclin dependent kinases 4 and 6 which bind cyclin D1 and reduces the magnitude of activation of cyclin E-Cdk2.

Deregulated expression of proto-oncogene c-MYC occurs in a broad range of human cancers and is often associated with poor prognosis, indicating a key role for this oncogene in tumour progression through transcription factor that regulates cell proliferation, growth and apoptosis. Dysregulated expression or function of c-Myc is one of the most common abnormalities in human malignancy. In the present invention, it is revealed that MPL acts on both these mediators of cell cycle transit (G1 to S), i.e. cyclin D1 and c-Myc.

The mTOR kinase controls the translation machinery, in response to amino acids and growth factors, via activation of p70 ribosomal S6 kinase (p70S6K) and inhibition of eIF-4E binding protein (4E-BP1).

As an important downstream effector of mTOR, S6K is involved in several cellular processes, including transcription and translation of proteins which mediate cell growth and metabolism. On this basis, the mTOR-S6K presents a critical axis for the translation of specific signals (growth factors, nutrients and hormones) into cellular response. Phosphorylation of p70 by mTOR is also critical for ribosome biogenesis.

The results shown in FIGS. 9 to 11 demonstrate MPL-induced inhibition of mTOR activation leading to down-regulation of p-mTOR, c-Myc [oncogene], cyclin D1, cyclin E2, cyclin dependent kinases 2 and 4 [essential for cell cycle progression] and p-P70S6K.

In summary, the present invention shows that MPL produces autophagy via the mTOR pathway and especially inhibits p-P70S6K (Thr 389) which is a downstream part of the mTOR signalling pathway known to regulate angiogenesis and autophagy.

The present invention also shows that MPL inhibits cyclin D1 which is necessary for cell cycle progression and is over expressed in many serious cancers. P70S6K down regulation has been shown by others to inhibit phosphorylation and thus activity of cyclin D1 which fits with the findings of the present invention. P70S6K also regulates PDCD4, focal adhesion kinase, E cadherin, B catenin and tissue transglutominate 2, which are important in metastasis and invasion.

The MPL/autophagy effect according to the present invention shows that MPL and similar AAD's is useful in treating diseases where autophagy is deficient, such as stroke, neurodegenerative diseases, a1 antitrypsin deficiencies, lysosomal storage disorders, cardiomyopathy, immune disorders and autoimmune disease, bacterial and viral infection, parasites, lipid disorders and even ageing. Further examples include Alzheimer's disease, Huntington's disease, age-related diseases, diseases related to transplant rejection, chronic inflammatory diseases, diseases related to glycogen storage, metastasis, systemic lupus, diseases related to inflammation and immune activation, anaemia, leucopenia, thrombocytopenia, diseases related to stent coatings, renal insufficiency, obesity, diabetes/insulin resistance, diseases related to non-alcoholic fatty liver, polycystic kidney, Parkinson's disease and fibrosis.

The present invention clearly shows that MPL produces autophagy (via the mTOR pathway) and so this may be a useful therapy other than for cancer.

The invention claimed is:

1. A method for the treatment of one or more mTOR pathway related diseases, the method comprising administering a therapeutically effective amount of a compound of formula (I):

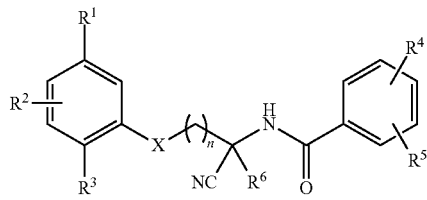

(I)

or a pharmaceutically acceptable salt or solvate thereof, to a patient in need thereof, wherein the one or more mTOR pathway related diseases is selected from neurodegenerative diseases, age-related diseases, diseases related to transplant rejection, chronic inflammatory diseases, diseases related to glycogen storage, systemic lupus, diseases related to inflammation and immune activation, anaemia, leucopenia, thrombocytopenia, diseases related to stent coatings, renal insufficiency, obesity, diabetes/insulin resistance, diseases related to non-alcoholic fatty liver, polycystic kidney, and fibrosis and wherein
   i) $R^1$ is alkyl, —$CF_3$ or —CN, $R^4$ is selected from H, alkyl, halogen, alkoxy, —$CF_3$, —$OCF_3$, —$SO_2$—$CF_3$, —SO—$CF_3$ or —S—$CF_3$ and $R^5$ is independently selected from H, alkyl, halogen, —$CF_3$ or —CN; or
   ii) $R^1$ is selected from H or halogen, $R^4$ is H, halogen, —S—$CF_3$, —$SOCF_3$ or —$SO_2CF_3$, and $R^5$ is independently selected from H, halogen, or —CN; and
$R^2$ and $R^3$ are each independently selected from H, alkyl, halogen, —$CF_3$ or —CN;
$R^6$ is independently selected from H, alkyl, halogen, alkoxy, —$CF_3$, —$OCF_3$, —$SO_2CF_3$, —$SOCF_3$ or —$SCF_3$;

X is heteroatom, N(alkyl) or NH; and
n is 1 to 20.

2. The method of claim 1, wherein,
$R^1$ is —CN, H or halogen;
$R^2$ is H or halogen;
$R^3$ is —$CF_3$ or halogen;
$R^4$ is —$SCF_3$, —$SOCF_3$, —$SO_2CF_3$, —$OCF_3$, or —$CF_3$;
$R^5$ is H;
$R^6$ is alkyl;
X is O; and
n is 1 to 5.

3. The method of claim 1, wherein $R^4$ is para to the amide moiety.

4. The method of claim 1, wherein the compound of formula (I) is the (R)- or (S)-enantiomer or the racemate.

5. The method of claim 1, wherein the compound of formula (I) is the (S)-enantiomer.

6. The method of claim 1, wherein the compound of formula (I) is selected from any one of the following compounds:

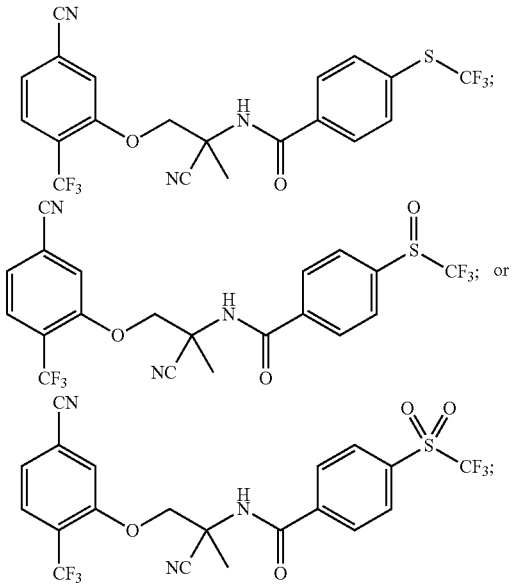

wherein each of the above compounds is the (R)- or (S)-enantiomer, or the racemate, or a pharmaceutically acceptable salt or solvate thereof.

7. The method of claim 1, wherein the compound of formula (I) is

AAD 2224 (MPL-(R))

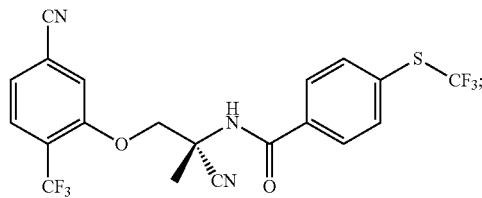

or a pharmaceutically acceptable salt or solvate thereof.

8. The method of claim 1, wherein the compound of formula (I) is MPL (N-[(1S)-1-cyano-2-(5-cyano-2-trifluoromethyl-phenoxy)-1-methyl-ethyl]-4-trifluoromethylsulfanyl-benzamide):

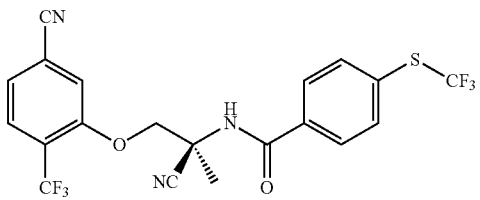

MPL or a pharmaceutically acceptable salt or solvate thereof.

9. The method of claim 1, wherein the compound of formula (I) is monepantel sulfone (MPL-SO$_2$):

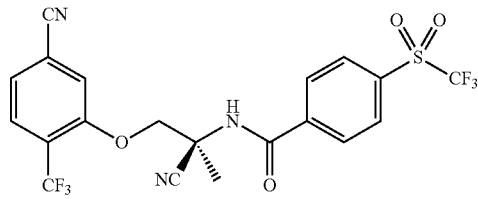

MPL-SO$_2$ or a pharmaceutically acceptable salt, solvate or prodrug thereof.

10. The method of claim 1, wherein the mTOR pathway related disease is chronic inflammatory disease.

11. The method according to claim 10, wherein the chronic inflammatory disease is rheumatoid arthritis or organ rejection after transplant.

12. The method of claim 1, wherein the mTOR pathway related disease is fibrosis.

13. The method according to claim 12, wherein the fibrosis is fibrosis of the liver, cardiac fibrosis or pulmonary fibrosis.

14. The method of claim 1, wherein the mTOR pathway related disease is neurodegenerative disease.

15. The method according to claim 14, wherein the neurodegenerative disease is Alzheimer's disease, Huntington's disease or Parkinson's disease.

16. The method according to claim 14, wherein the neurodegenerative disease is Parkinson's disease.

17. The method according to claim 14, wherein the neurodegenerative disease is Huntington's disease.

18. The method according to claim 14, wherein the neurodegenerative disease is Alzheimer's disease.

19. The method of claim 1 wherein the therapeutically effective amount of a compound of formula (I) is administered in a pharmaceutical composition comprising at least one pharmaceutically acceptable carrier.

* * * * *